(12) United States Patent
Vidlund et al.

(10) Patent No.: US 10,653,522 B1
(45) Date of Patent: May 19, 2020

(54) PROXIMAL TAB FOR SIDE-DELIVERED TRANSCATHETER HEART VALVE PROSTHESIS

(71) Applicant: VDYNE, LLC, Maple Grove, MN (US)

(72) Inventors: Robert Vidlund, Forest Lake, MN (US); Mark Christianson, Plymouth, MN (US); Neelakantan Saikrishnan, Plymouth, MN (US)

(73) Assignee: VDYNE, INC., Maple Grove, MN (US)

( * ) Notice: Subject to any disclaimer, the term of this patent is extended or adjusted under 35 U.S.C. 154(b) by 0 days.

(21) Appl. No.: 16/455,417

(22) Filed: Jun. 27, 2019

Related U.S. Application Data

(60) Provisional application No. 62/782,350, filed on Dec. 20, 2018.

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2/2442* (2013.01); *A61F 2210/0014* (2013.01); *A61F 2220/0016* (2013.01); *A61F 2250/0039* (2013.01)

(58) Field of Classification Search
CPC ........ A61F 2/24; A61F 2/2409; A61F 2/2418; A61F 2/143; A61F 2/2436; A61F 2/243
See application file for complete search history.

(56) References Cited

U.S. PATENT DOCUMENTS

| | | | |
|---|---|---|---|
| 5,397,351 | A | 3/1995 | Pavcnik |
| 6,197,013 | B1 | 3/2001 | Reed |
| 6,582,467 | B1 | 6/2003 | Teitelbaum |
| 7,074,189 | B1 | 7/2006 | Montegrande |
| 7,125,418 | B2 | 10/2006 | Duran |
| 7,331,991 | B2 | 2/2008 | Kheradvar |
| 7,374,571 | B2 | 5/2008 | Pease |
| 7,449,027 | B2 | 11/2008 | Hunt |
| 7,717,952 | B2 | 5/2010 | Case |
| 7,753,949 | B2 | 7/2010 | Lamphere |
| 7,828,840 | B2 | 11/2010 | Biggs |
| 7,846,199 | B2 | 12/2010 | Paul |
| 8,303,648 | B2 | 11/2012 | Grewe |
| 8,366,768 | B2 | 2/2013 | Zhang |
| 8,491,650 | B2 | 7/2013 | Wiemeyer |
| 8,568,474 | B2 | 10/2013 | Yeung |

(Continued)

*Primary Examiner* — Katherine M Shi
*Assistant Examiner* — Lindsey Bachman
(74) *Attorney, Agent, or Firm* — Juneau & Mitchell IP Law Firm; Todd L. Juneau

(57) ABSTRACT

The invention relates to a transcatheter heart valve replacement (A61F2/2412), and in particular Compression Capable Annular Frames for a side delivered transcatheter prosthetic heart valve having a annular support frame having compressible wire cells that facilitate rolling and folding the valve length-wise, or orthogonally to the central axis of the flow control component, allowing a very large diameter valve to be delivered and deployed to the tricuspid valve from the inferior vena cava or superior vena cava, or trans-atrially to the mitral valve, the valve having a height of about 5-60 mm and a diameter of about 25-80 mm, without requiring an oversized diameter catheter and without requiring delivery and deployment from a catheter at an acute angle of approach.

5 Claims, 17 Drawing Sheets

(56) References Cited

U.S. PATENT DOCUMENTS

| | | |
|---|---|---|
| 8,641,752 B1 | 2/2014 | Holm |
| 8,696,743 B2 | 4/2014 | Holecek |
| 8,728,153 B2 | 5/2014 | Bishop |
| 8,758,395 B2 | 6/2014 | Kleshinski |
| 8,846,390 B2 | 9/2014 | Dove |
| 8,876,892 B2 | 11/2014 | Tran |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer |
| 8,956,404 B2 | 2/2015 | Börtlein |
| 9,011,524 B2 | 4/2015 | Eberhardt |
| 9,017,399 B2 | 4/2015 | Gross |
| 9,050,188 B2 | 4/2015 | Schweich |
| 9,072,604 B1 | 7/2015 | Melnick |
| 9,119,714 B2 | 9/2015 | Shandas |
| 9,216,076 B2 | 12/2015 | Mitra |
| 9,241,792 B2 | 1/2016 | Benichou |
| 9,248,016 B2 | 2/2016 | Oba |
| 9,259,215 B2 | 2/2016 | Chou |
| 9,277,990 B2 | 3/2016 | Klima |
| 9,289,282 B2 | 3/2016 | Olson |
| 9,289,296 B2 | 3/2016 | Braido |
| 9,295,547 B2 | 3/2016 | Costello |
| 9,301,839 B2 | 4/2016 | Stante |
| 9,456,899 B2 | 4/2016 | Yeung |
| 9,339,367 B2 | 5/2016 | Carpenter |
| 9,370,418 B2 | 6/2016 | Pintor |
| 9,381,083 B2 | 7/2016 | Costello |
| 9,387,075 B2 | 7/2016 | Börtlein |
| 9,393,111 B2 | 7/2016 | Ma |
| 9,433,500 B2 | 9/2016 | Chau |
| 9,440,054 B2 | 9/2016 | Bishop |
| 9,474,604 B2 | 10/2016 | Centola |
| 9,486,306 B2 | 11/2016 | Tegels |
| 9,510,941 B2 | 12/2016 | Bishop |
| 9,554,902 B2 | 1/2017 | Braido |
| 9,579,196 B2 | 2/2017 | Morriss |
| 9,579,200 B2 | 2/2017 | Lederman |
| 9,610,159 B2 | 4/2017 | Christianson |
| 9,615,925 B2 | 4/2017 | Subramanian |
| 9,629,719 B2 | 4/2017 | Rothstein |
| 9,636,222 B2 | 5/2017 | Oslund |
| 9,649,191 B2 | 5/2017 | Savage |
| 9,662,203 B2 | 5/2017 | Sheehan |
| 9,662,209 B2 | 5/2017 | Gross |
| 9,675,454 B2 | 6/2017 | Vidlund |
| 9,675,485 B2 | 6/2017 | Essinger |
| 9,687,343 B2 | 6/2017 | Börtlein |
| 9,707,076 B2 | 7/2017 | Stack |
| 9,713,530 B2 | 7/2017 | Cabiri |
| 9,750,607 B2 | 9/2017 | Ganesan |
| 9,763,778 B2 | 9/2017 | Börtlein |
| 9,763,779 B2 | 9/2017 | Börtlein |
| 9,839,511 B2 | 12/2017 | Ma |
| 9,849,011 B2 | 12/2017 | Zimmerman |
| 9,855,384 B2 | 1/2018 | Cohen |
| 9,861,464 B2 | 1/2018 | Azimpour |
| 9,895,219 B2 | 2/2018 | Costello |
| 9,901,330 B2 | 2/2018 | Akpinar |
| 9,918,838 B2 | 3/2018 | Ring |
| 9,943,409 B2 | 4/2018 | Kim |
| 9,949,825 B2 | 4/2018 | Braido |
| 9,968,444 B2 | 5/2018 | Millwee |
| 9,968,445 B2 | 5/2018 | Morriss |
| 9,980,815 B2 | 5/2018 | Nitzan |
| 9,987,121 B2 | 6/2018 | Blanzy |
| 1,002,882 A1 | 7/2018 | Centola |
| 10,010,411 B2 | 7/2018 | Peter |
| 10,010,412 B2 | 7/2018 | Taft |
| 10,022,054 B2 | 7/2018 | Najafi |
| 10,022,222 B2 | 7/2018 | Groothuis |
| 10,022,223 B2 | 7/2018 | Bruchman |
| 10,028,821 B2 | 7/2018 | Centola |
| 10,028,831 B2 | 7/2018 | Morin |
| 10,034,667 B2 | 7/2018 | Morris |
| 10,034,747 B2 | 7/2018 | Harewood |
| 10,039,638 B2 | 8/2018 | Bruchman |
| 10,058,315 B2 | 8/2018 | Rafiee |
| 10,058,411 B2 | 8/2018 | Fifer |
| 10,058,421 B2 | 8/2018 | Eberhardt et al. |
| 10,058,426 B2 | 8/2018 | Barbarino |
| 10,064,405 B2 | 9/2018 | Dale |
| 10,080,653 B2 | 9/2018 | Conklin |
| 10,085,835 B2 | 10/2018 | Thambar |
| 10,105,224 B2 | 10/2018 | Buchbinder |
| 10,117,741 B2 | 11/2018 | Schweich |
| 10,123,874 B2 | 11/2018 | Khairkhahan |
| 10,130,331 B2 | 11/2018 | Stigall |
| 10,130,467 B2 | 11/2018 | Braido |
| 10,149,685 B2 | 12/2018 | Kizuka |
| 10,154,905 B2 | 12/2018 | Duffy |
| 10,179,043 B2 | 1/2019 | Cohen-Tzemach |
| 10,182,908 B2 | 1/2019 | Tubishevitz |
| 10,182,911 B2 | 1/2019 | Hilukka |
| 10,206,775 B2 | 2/2019 | Kovalsky |
| 10,219,895 B2 | 3/2019 | Wagner |
| 10,219,896 B2 | 3/2019 | Sandstrom |
| 10,220,192 B2 | 3/2019 | Drasler |
| 10,226,178 B2 | 3/2019 | Cohen |
| 10,226,335 B2 | 3/2019 | Cartledge |
| 10,245,142 B2 | 4/2019 | Bonhoeffer |
| 10,258,467 B2 | 4/2019 | Hou |
| 10,265,173 B2 | 4/2019 | Griffin |
| 10,321,987 B2 | 6/2019 | Wang |
| 10,321,995 B1 | 6/2019 | Christianson |
| 10,327,895 B2 | 6/2019 | Lozonschi |
| 10,327,899 B2 | 6/2019 | Sandstrom |
| 10,329,066 B2 | 6/2019 | Kruetzfeldt |
| 10,350,047 B2 | 7/2019 | Rajpara |
| 10,357,361 B2 | 7/2019 | Rafi |
| 10,368,989 B2 | 8/2019 | Duffy |
| 10,398,550 B2 | 9/2019 | Chalekian |
| 10,426,611 B2 | 10/2019 | Hariton |
| 10,433,957 B2 | 10/2019 | Khouengboua |
| 10,433,960 B1 | 10/2019 | Sutherland |
| 2003/0040772 A1 | 2/2003 | Hyodoh |
| 2003/0153901 A1 | 8/2003 | Herweck |
| 2003/0166990 A1 | 9/2003 | Trauthen |
| 2003/0171801 A1 | 9/2003 | Bates |
| 2006/0015167 A1 | 1/2006 | Armstrong |
| 2006/0195180 A1 | 8/2006 | Kheradvar |
| 2006/0271098 A1 | 11/2006 | Peacock |
| 2007/0027535 A1 | 2/2007 | Purdy |
| 2007/0032850 A1 | 2/2007 | Ruiz |
| 2007/0038295 A1 | 2/2007 | Case |
| 2007/0162102 A1 | 7/2007 | Ryan |
| 2007/0208417 A1 | 9/2007 | Agnew |
| 2007/0213805 A1 | 9/2007 | Schaeffer |
| 2007/0233176 A1 | 10/2007 | Gilsen |
| 2007/0233228 A1 | 10/2007 | Eberhardt |
| 2007/0288087 A1 | 12/2007 | Fearnot |
| 2008/0004686 A1 | 1/2008 | Hunt |
| 2008/0020013 A1 | 1/2008 | Reyes |
| 2008/0132999 A1 | 6/2008 | Mericle |
| 2008/0200977 A1 | 8/2008 | Paul |
| 2008/0208332 A1 | 8/2008 | Lamphere |
| 2008/0262609 A1 | 10/2008 | Gross |
| 2008/0275550 A1 | 11/2008 | Kheradvar |
| 2009/0192586 A1 | 7/2009 | Tabor |
| 2009/0254174 A1 | 10/2009 | Case |
| 2009/0264991 A1 | 10/2009 | Paul |
| 2009/0094189 A1 | 11/2009 | Macauley |
| 2009/0287290 A1 | 11/2009 | Macaulay |
| 2010/0160773 A1 | 6/2010 | Cohen |
| 2010/0161043 A1 | 6/2010 | Maisano |
| 2010/0168844 A1 | 7/2010 | Toomes |
| 2010/0174363 A1 | 7/2010 | Castro |
| 2010/0179583 A1 | 7/2010 | Carpenter |
| 2010/0179584 A1 | 7/2010 | Carpenter |
| 2010/0179647 A1 | 7/2010 | Carpenter |
| 2010/0305685 A1 | 12/2010 | Millwee |
| 2011/0029071 A1 | 2/2011 | Zlotnick |

(56) References Cited

U.S. PATENT DOCUMENTS

| | | |
|---|---|---|
| 2011/0098804 A1 | 4/2011 | Yeung |
| 2011/0125145 A1 | 5/2011 | Mody |
| 2011/0172764 A1 | 7/2011 | Badhwar |
| 2011/0245917 A1 | 10/2011 | Savage |
| 2011/0251675 A1 | 10/2011 | Dwork |
| 2011/0257721 A1 | 10/2011 | Tabor |
| 2012/0022633 A1 | 1/2012 | Olson |
| 2012/0022640 A1 | 1/2012 | Gross |
| 2012/0022644 A1 | 1/2012 | Reich |
| 2012/0035701 A1 | 2/2012 | To |
| 2012/0123531 A1 | 5/2012 | Tsukashima |
| 2012/0137521 A1 | 6/2012 | Millwee |
| 2012/0172981 A1 | 7/2012 | DuMontelle |
| 2012/0209375 A1 | 8/2012 | Madrid |
| 2012/0232574 A1 | 9/2012 | Kim |
| 2012/0277853 A1 | 11/2012 | Rothstein |
| 2013/0055941 A1 | 3/2013 | Holecek |
| 2013/0131714 A1 | 5/2013 | Wang |
| 2013/0131792 A1 | 5/2013 | Miller |
| 2013/0166017 A1 | 6/2013 | Cartledge |
| 2013/0184742 A1 | 7/2013 | Ganesan |
| 2013/0190857 A1 | 7/2013 | Mitra |
| 2013/0197621 A1 | 8/2013 | Ryan |
| 2013/0226289 A1 | 8/2013 | Shaolian |
| 2013/0238010 A1 | 9/2013 | Johnson |
| 2013/0253570 A1 | 9/2013 | Bates |
| 2013/0274618 A1 | 10/2013 | Hou |
| 2013/0274855 A1 | 10/2013 | Stante |
| 2013/0282110 A1 | 10/2013 | Schweich |
| 2013/0297010 A1 | 11/2013 | Bishop |
| 2013/0331929 A1 | 12/2013 | Mitra |
| 2014/0000112 A1 | 1/2014 | Braido |
| 2014/0005540 A1 | 1/2014 | Merhi |
| 2014/0005768 A1 | 1/2014 | Thomas |
| 2014/0039511 A1 | 2/2014 | Morris |
| 2014/0081383 A1 | 3/2014 | Eberhardt |
| 2014/0088680 A1 | 3/2014 | Costello |
| 2014/0107758 A1 | 4/2014 | Glazier |
| 2014/0110279 A1 | 4/2014 | Kruetzfeldt |
| 2014/0114403 A1 | 4/2014 | Dale |
| 2014/0135895 A1 | 5/2014 | Andress |
| 2014/0172070 A1 | 6/2014 | Seguin |
| 2014/0180069 A1 | 6/2014 | Millett |
| 2014/0180070 A1 | 6/2014 | Millett |
| 2014/0194704 A1 | 7/2014 | Millett |
| 2014/0214069 A1 | 7/2014 | Franklin |
| 2014/0214159 A1 | 7/2014 | Vidlund |
| 2014/0222137 A1 | 8/2014 | Miller |
| 2014/0249566 A1 | 9/2014 | Quinn |
| 2014/0276616 A1 | 9/2014 | Smith |
| 2014/0276971 A1 | 9/2014 | Kovach |
| 2014/0277388 A1 | 9/2014 | Skemp |
| 2014/0277408 A1 | 9/2014 | Folan |
| 2014/0296969 A1 | 10/2014 | Tegels |
| 2014/0303718 A1 | 10/2014 | Tegels |
| 2014/0303724 A1 | 10/2014 | Bluestein |
| 2014/0309732 A1 | 10/2014 | Solem |
| 2014/0324161 A1 | 10/2014 | Tegels |
| 2014/0350662 A1 | 11/2014 | Vaturi |
| 2014/0371789 A1 | 12/2014 | Harton |
| 2014/0379076 A1 | 12/2014 | Vidlund |
| 2015/0005808 A1 | 1/2015 | Chouinard |
| 2015/0005874 A1 | 1/2015 | Vidlund |
| 2015/0039081 A1* | 2/2015 | Costello ............ A61F 2/2412 623/2.11 |
| 2015/0051687 A1 | 2/2015 | Dickerhoff |
| 2015/0094802 A1 | 4/2015 | Buchbinder |
| 2015/0112188 A1 | 4/2015 | Stigall |
| 2015/0119982 A1 | 4/2015 | Quill |
| 2015/0127093 A1 | 5/2015 | Hosmer |
| 2015/0142103 A1 | 5/2015 | Vidlund |
| 2015/0196391 A1 | 7/2015 | Dwork |
| 2015/0202044 A1 | 7/2015 | Chau |
| 2015/0216661 A1 | 8/2015 | Hacohen |
| 2015/0230919 A1 | 8/2015 | Chau |
| 2015/0245934 A1 | 9/2015 | Lombardi |
| 2015/0257880 A1 | 9/2015 | Börtlein |
| 2015/0257882 A1 | 9/2015 | Börtlein |
| 2015/0272731 A1 | 10/2015 | Racchini |
| 2015/0289971 A1 | 10/2015 | Costello |
| 2015/0289975 A1 | 10/2015 | Costello |
| 2015/0297241 A1 | 10/2015 | Yodfat |
| 2015/0305867 A1 | 10/2015 | Liu |
| 2015/0313701 A1 | 11/2015 | Krahbichler |
| 2015/0342717 A1 | 12/2015 | O'Donnell |
| 2015/0351904 A1 | 12/2015 | Cooper |
| 2015/0359629 A1 | 12/2015 | Ganesan |
| 2016/0008130 A1 | 1/2016 | Hasin |
| 2016/0022417 A1 | 1/2016 | Karapetian |
| 2016/0030165 A1 | 2/2016 | Mitra |
| 2016/0030167 A1 | 2/2016 | Delaloye |
| 2016/0038283 A1 | 2/2016 | Divekar |
| 2016/0045165 A1 | 2/2016 | Braido |
| 2016/0045306 A1 | 2/2016 | Agrawal |
| 2016/0045309 A1 | 2/2016 | Valdez |
| 2016/0067031 A1 | 3/2016 | Kassab |
| 2016/0081799 A1 | 3/2016 | Leo |
| 2016/0095703 A1 | 4/2016 | Thomas |
| 2016/0095704 A1 | 4/2016 | Whitman |
| 2016/0113764 A1 | 4/2016 | Sheahan |
| 2016/0113766 A1 | 4/2016 | Ganesan |
| 2016/0113768 A1 | 4/2016 | Ganesan |
| 2016/0143721 A1 | 5/2016 | Rosenbluth |
| 2016/0143730 A1 | 5/2016 | Kheradvar |
| 2016/0143735 A1 | 5/2016 | Subramanian |
| 2016/0143739 A1 | 5/2016 | Horgan |
| 2016/0158004 A1 | 6/2016 | Kumar |
| 2016/0158007 A1 | 6/2016 | Centola |
| 2016/0158008 A1 | 6/2016 | Miller |
| 2016/0166382 A1 | 6/2016 | Nguyen |
| 2016/0184488 A1 | 6/2016 | Toyoda |
| 2016/0194425 A1 | 7/2016 | Mitra |
| 2016/0213470 A1 | 7/2016 | Ahlberg |
| 2016/0220367 A1 | 8/2016 | Barrett |
| 2016/0220372 A1 | 8/2016 | Medema |
| 2016/0220734 A1 | 8/2016 | Dyamenahalli |
| 2016/0228250 A1 | 8/2016 | Casley |
| 2016/0235530 A1 | 8/2016 | Thomas |
| 2016/0256269 A1 | 9/2016 | Cahalane |
| 2016/0256270 A1 | 9/2016 | Folan |
| 2016/0270911 A1 | 9/2016 | Ganesan |
| 2016/0303804 A1 | 10/2016 | Grbic |
| 2016/0310274 A1 | 10/2016 | Gross |
| 2016/0317301 A1 | 11/2016 | Quadri |
| 2016/0324639 A1 | 11/2016 | Nguyen |
| 2016/0331534 A1 | 11/2016 | Buchbinder |
| 2016/0354201 A1 | 12/2016 | Keough |
| 2016/0361169 A1 | 12/2016 | Gross |
| 2016/0361184 A1 | 12/2016 | Tabor |
| 2016/0367364 A1 | 12/2016 | Torrianni |
| 2017/0000603 A1 | 1/2017 | Conklin |
| 2017/0000604 A1 | 1/2017 | Conklin |
| 2017/0035562 A1 | 2/2017 | Quadri |
| 2017/0056171 A1 | 3/2017 | Cooper |
| 2017/0071736 A1 | 3/2017 | Zhu |
| 2017/0076014 A1 | 3/2017 | Bressloff |
| 2017/0079786 A1 | 3/2017 | Li |
| 2017/0079795 A1 | 3/2017 | Morrissey |
| 2017/0100246 A1 | 4/2017 | Rust |
| 2017/0112620 A1 | 4/2017 | Curley |
| 2017/0128208 A1 | 5/2017 | Christianson |
| 2017/0143488 A1 | 5/2017 | Lashinski |
| 2017/0143489 A1 | 5/2017 | Lashinski |
| 2017/0165065 A1 | 6/2017 | Rothstein |
| 2017/0181851 A1 | 6/2017 | Annest |
| 2017/0189177 A1 | 7/2017 | Schweich |
| 2017/0196690 A1 | 7/2017 | Racchini |
| 2017/0209266 A1 | 7/2017 | Lane |
| 2017/0216026 A1* | 8/2017 | Quill ............... A61F 2/2418 |
| 2017/0216030 A1 | 8/2017 | Joensson |
| 2017/0224480 A1 | 8/2017 | Garde |
| 2017/0224486 A1 | 8/2017 | Delaloye |
| 2017/0231755 A1 | 8/2017 | Gloss |
| 2017/0231760 A1 | 8/2017 | Lane |

(56) References Cited

U.S. PATENT DOCUMENTS

| | | |
|---|---|---|
| 2017/0239047 A1 | 8/2017 | Quill |
| 2017/0245994 A1 | 8/2017 | Khairkhahan |
| 2017/0252163 A1 | 9/2017 | Kheradvar |
| 2017/0258584 A1 | 9/2017 | Chang |
| 2017/0258585 A1 | 9/2017 | Marquez |
| 2017/0273784 A1 | 9/2017 | Racchini |
| 2017/0281337 A1 | 10/2017 | Campbell |
| 2017/0296340 A1 | 10/2017 | Gross |
| 2017/0325976 A1 | 11/2017 | Nguyen |
| 2017/0333184 A1 | 11/2017 | Ryan |
| 2017/0348099 A1 | 12/2017 | Mendelson |
| 2017/0348100 A1 | 12/2017 | Lane |
| 2017/0360558 A1 | 12/2017 | Ma |
| 2017/0360561 A1 | 12/2017 | Bell |
| 2018/0035971 A1 | 2/2018 | Brenner |
| 2018/0042549 A1 | 2/2018 | Ho |
| 2018/0042723 A1 | 2/2018 | Yellin |
| 2018/0043133 A1 | 2/2018 | Wong |
| 2018/0049875 A1 | 2/2018 | Iflah |
| 2018/0049876 A1 | 2/2018 | Mikraki |
| 2018/0055628 A1 | 3/2018 | Patel |
| 2018/0055633 A1 | 3/2018 | Costello |
| 2018/0056045 A1 | 3/2018 | Donoghue |
| 2018/0056046 A1 | 3/2018 | Kiersey |
| 2018/0071088 A1 | 3/2018 | Badhwar |
| 2018/0078367 A1 | 3/2018 | Saar |
| 2018/0078368 A1 | 3/2018 | Vidlund |
| 2018/0078370 A1 | 3/2018 | Kovalsky |
| 2018/0085219 A1 | 3/2018 | Krivoruchko |
| 2018/0098837 A1 | 4/2018 | Shahriari |
| 2018/0099124 A1 | 4/2018 | McLoughlin |
| 2018/0116843 A1 | 5/2018 | Schreck |
| 2018/0125642 A1 | 5/2018 | White |
| 2018/0125654 A1 | 5/2018 | Duffy |
| 2018/0126127 A1 | 5/2018 | Devereoux |
| 2018/0133000 A1 | 5/2018 | Scheinblum |
| 2018/0133006 A1 | 5/2018 | Jones |
| 2018/0133011 A1 | 5/2018 | Perouse |
| 2018/0140417 A1 | 5/2018 | Sciscio |
| 2018/0147041 A1 | 5/2018 | Chouinard |
| 2018/0161158 A1 | 6/2018 | Kovalsky |
| 2018/0161161 A1 | 6/2018 | Yellin |
| 2018/0168793 A1 | 6/2018 | Lees |
| 2018/0177580 A9 | 6/2018 | Shemesh |
| 2018/0177594 A1 | 6/2018 | Patel |
| 2018/0185153 A1 | 7/2018 | Bishop |
| 2018/0193138 A1 | 7/2018 | Vidlund |
| 2018/0214141 A1 | 8/2018 | Mendez |
| 2018/0221016 A1 | 8/2018 | Conklin |
| 2018/0243071 A1 | 8/2018 | Eigler |
| 2018/0243532 A1 | 8/2018 | Willard |
| 2018/0256322 A1 | 9/2018 | Zhang |
| 2018/0256327 A1 | 9/2018 | Perszyk |
| 2018/0280174 A1 | 10/2018 | Dwork |
| 2018/0289474 A1 | 10/2018 | Rajagopal |
| 2018/0289475 A1 | 10/2018 | Chung |
| 2018/0289485 A1 | 10/2018 | Rajagopal |
| 2018/0296335 A1 | 10/2018 | Miyashiro |
| 2018/0296337 A1 | 10/2018 | Duhay |
| 2018/0303488 A1 | 10/2018 | Hill |
| 2018/0311474 A1 | 11/2018 | Tyler |
| 2018/0318073 A1 | 11/2018 | Tseng |
| 2018/0318078 A1 | 11/2018 | Willard |
| 2018/0325665 A1 | 11/2018 | Gurovich |
| 2018/0325671 A1 | 11/2018 | Abunassar |
| 2018/0338832 A1 | 11/2018 | Ganesan |
| 2018/0353293 A1 | 12/2018 | Colavito |
| 2018/0353295 A1 | 12/2018 | Cooper |
| 2018/0360439 A1 | 12/2018 | Niland |
| 2018/0360599 A1 | 12/2018 | Drasler |
| 2019/0008640 A1 | 1/2019 | Cooper |
| 2019/0015188 A1 | 1/2019 | Eigler |
| 2019/0021834 A1 | 1/2019 | Nir |
| 2019/0029823 A1 | 1/2019 | Nguyen |
| 2019/0038404 A1 | 2/2019 | Iamberger |
| 2019/0038405 A1 | 2/2019 | Iamberger |
| 2019/0053894 A1 | 2/2019 | Levi |
| 2019/0053895 A1 | 2/2019 | Levi |
| 2019/0053897 A1 | 2/2019 | Levi |
| 2019/0053898 A1 | 2/2019 | Maimon |
| 2019/0053899 A1 | 2/2019 | Levi |
| 2019/0060051 A1 | 2/2019 | Scheeff |
| 2019/0060059 A1 | 2/2019 | Delgado |
| 2019/0060069 A1 | 2/2019 | Maimon |
| 2019/0060071 A1 | 2/2019 | Lane |
| 2019/0070003 A1 | 3/2019 | Siegel |
| 2019/0076233 A1 | 3/2019 | Fish |
| 2019/0076249 A1 | 3/2019 | Khairkhahan |
| 2019/0083085 A1 | 3/2019 | Gilmore |
| 2019/0091005 A1 | 3/2019 | Fifer |
| 2019/0091015 A1 | 3/2019 | Dienno |
| 2019/0091018 A1 | 3/2019 | Hariton |
| 2019/0091022 A1 | 3/2019 | Yellin |
| 2019/0099265 A1 | 4/2019 | Braido |
| 2019/0099270 A1 | 4/2019 | Morrissey |
| 2019/0105153 A1 | 4/2019 | Barash |
| 2019/0117223 A1 | 4/2019 | Abunassar |
| 2019/0117387 A1 | 4/2019 | Li |
| 2019/0117391 A1 | 4/2019 | Humair |
| 2019/0117400 A1 | 4/2019 | Medema |
| 2019/0117401 A1 | 4/2019 | Cortez |
| 2019/0125287 A1 | 5/2019 | Itou |
| 2019/0125536 A1 | 5/2019 | Prabhu |
| 2019/0133528 A1 | 5/2019 | Kassab |
| 2019/0133756 A1 | 5/2019 | Zhang |
| 2019/0133757 A1 | 5/2019 | Zhang |
| 2019/0133765 A1 | 5/2019 | Yellin |
| 2019/0142566 A1 | 5/2019 | Lansky |
| 2019/0142582 A1 | 5/2019 | Drasler |
| 2019/0150867 A1 | 5/2019 | Itou |
| 2019/0151509 A1 | 5/2019 | Kheradvar |
| 2019/0167423 A1 | 6/2019 | Hariton |
| 2019/0167429 A1 | 6/2019 | Stearns |
| 2019/0175338 A1 | 6/2019 | White |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp |
| 2019/0192287 A1 | 6/2019 | Sandstrom |
| 2019/0192296 A1 | 6/2019 | Schwartz |
| 2019/0209317 A1 | 7/2019 | Zhang |
| 2019/0209320 A1 | 7/2019 | Drasler |
| 2019/0231523 A1 | 8/2019 | Lombardi |
| 2019/0240020 A1 | 8/2019 | Rafiee |
| 2019/0240022 A1 | 8/2019 | Rafiee |
| 2019/0247050 A1 | 8/2019 | Goldsmith |
| 2019/0254815 A1 | 8/2019 | Bruchman |
| 2019/0254816 A1 | 8/2019 | Anderson |
| 2019/0262118 A1 | 8/2019 | Eigler |
| 2019/0262129 A1 | 8/2019 | Cooper |
| 2019/0269413 A1 | 9/2019 | Yodfat |
| 2019/0269504 A1 | 9/2019 | Wang |
| 2019/0269839 A1 | 9/2019 | Wilson |
| 2019/0282360 A1 | 9/2019 | Colavito |
| 2019/0290426 A1 | 9/2019 | Maimon |
| 2019/0290427 A1 | 9/2019 | Mantanus |
| 2019/0307563 A1 | 10/2019 | Sandstrom |
| 2019/0307589 A1 | 10/2019 | Goldberg |

\* cited by examiner septal side proximal view septal side distal view septal view 136 compressed valve — IVC partial expansion — IVC

PA — IVC 275 proximal pre-release tab

PA — IVC 270 post-release proximal tab 136 compressed laser cut partial expansion 275 proximal tab pre-release 270 proximal tab, released pushing tube expels valve from catheter, delivers distal tab to rvot proximal side of valve rotates down into annulus, transitioning flow to prostheses proximal tab released, extends into subannular space proximal tab attached to septal perimeter wall anterior side septal side

FIG. 35
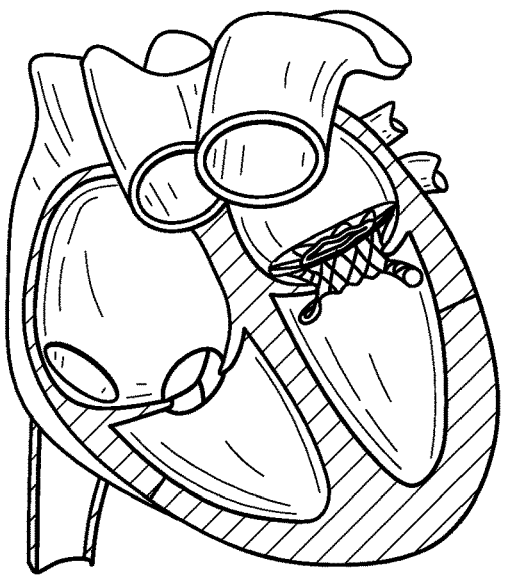
mitral prosthesis, subannular tabs - anterolateral, postero-medial
FIG. 36  top view
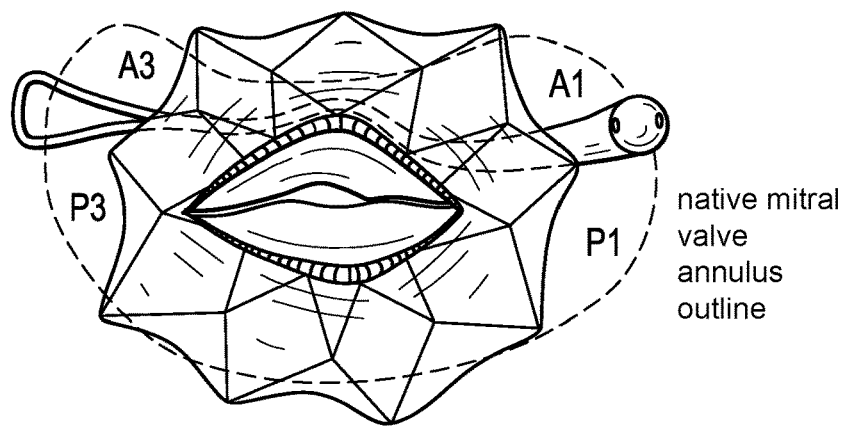
native mitral valve annulus outline
FIG. 37
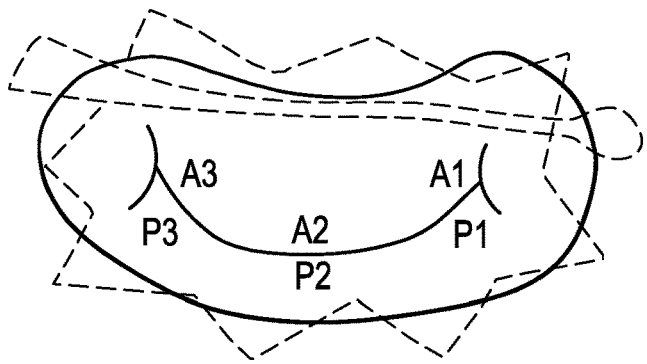

side view - from anterior mitral annulus open hinged 270 proximal tab 275 compressed (bent) spring release proximal tab

275

FIG. 44 top view
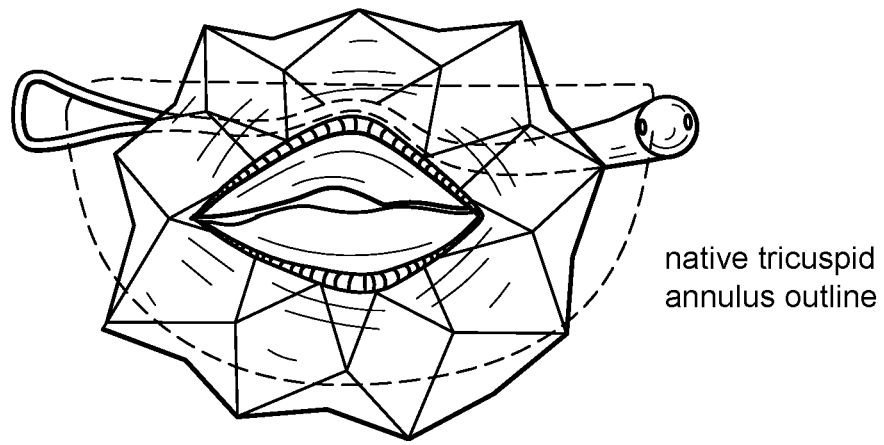
native tricuspid annulus outline
FIG. 45
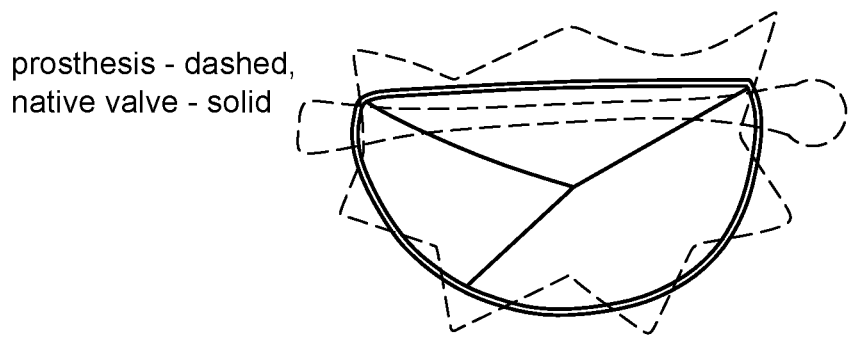
prosthesis - dashed, native valve - solid
FIG. 46
multiple subannular tabs
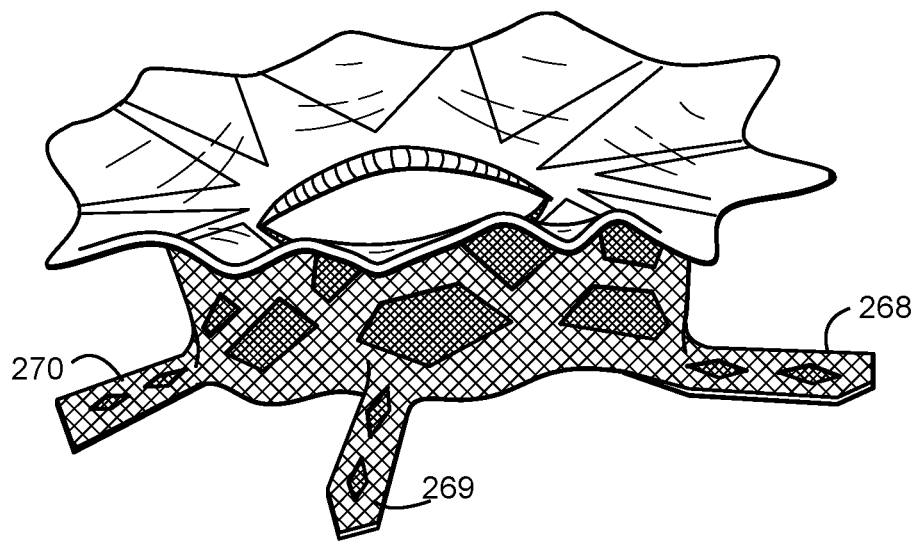

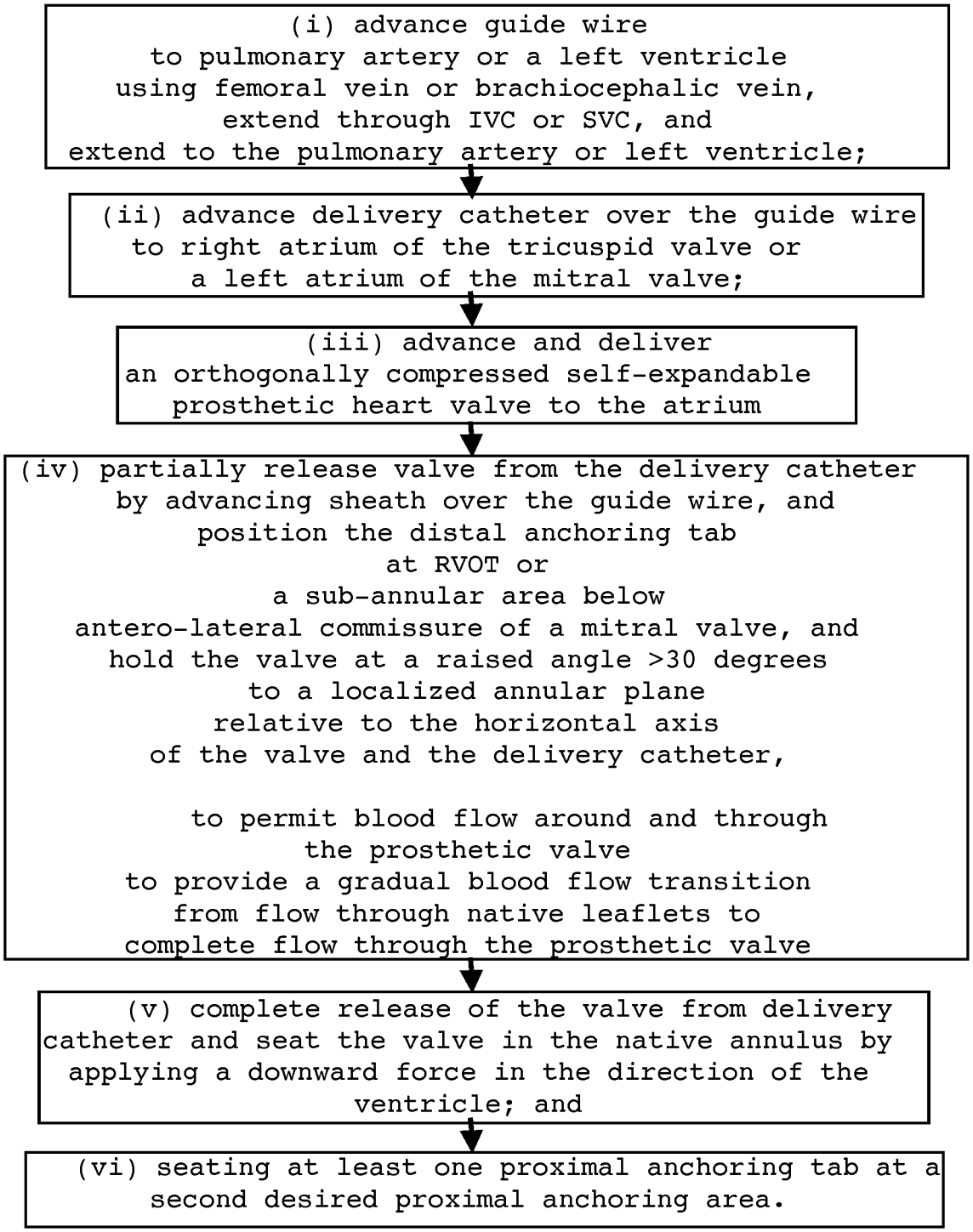

PROXIMAL TAB FOR SIDE-DELIVERED TRANSCATHETER HEART VALVE PROSTHESIS

CROSS-REFERENCE TO RELATED APPLICATIONS

Provided by Application Data Sheet per USPTO rules.

STATEMENT REGARDING FEDERALLY SPONSORED R&D

Provided by Application Data Sheet per with USPTO rules.

NAMES OF PARTIES TO JOINT RESEARCH AGREEMENT

Provided by Application Data Sheet per with USPTO rules.

REFERENCE TO SEQUENCE LISTING

Provided by Application Data Sheet per USPTO rules.

STATEMENT RE PRIOR DISCLOSURES

Provided by Application Data Sheet per USPTO rules.

BACKGROUND OF THE INVENTION

Field of the Invention

The invention relates to a transcatheter heart valve replacement (A61F2/2412).

Description of the Related Art

In 1952 surgeons implanted the first mechanical heart valve, a ball valve that could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting dic technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The present invention is directed to a transcatheter heart valve replacement (A61F2/2412), having a proximal sub-annular anchoring tab and a distal sub-annular anchoring tab, and in particular an orthogonally (length-wise) delivered transcatheter prosthetic heart valve having a annular support frame having compressible wire cells that facilitate rolling, folding, compressing in height and.or width, the valve length-wise, or orthogonal, to the central axis of the flow control component, allowing a very large diameter valve to be delivered and deployed from the inferior vena cava directly into the tricuspid valve, e.g. has a height of about 5-60 mm and a diameter of about 25-80 mm, without requiring an oversized diameter catheter and without requiring delivery and deployment from a catheter at an acute angle of approach.

Side Delivered Valve

Accordingly, the present invention is directed to a side delivered transcatheter prosthetic heart valve having a distal anchoring tab and a proximal anchoring tab, comprising:
(i) a self-expanding annular support frame, said annular support frame having a central channel and an outer perimeter wall circumscribing a central vertical axis in an expanded configuration, said annular support frame having a distal side and a proximal side,
(ii) a flow control component mounted within the annular support frame and configured to permit blood flow in a first direction through an inflow end of the valve and block blood flow in a second direction, opposite the first direction, through an outflow end of the valve,
(iii) a distal anchoring tab mounted on the distal side of the annular support frame,
(iv) a proximal anchoring tab mounted on the proximal side of the annular support frame,
wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a length-wise cylindrical axis of the delivery catheter,
wherein the valve has a height of about 5-60 mm and a diameter of about 25-80 mm.

In another preferred embodiment of the invention, there is provided a valve wherein the annular support frame is comprised of a plurality of compressible wire cells having a orientation and cell geometry substantially orthogonal to the central vertical axis to minimize wire cell strain when the annular support frame is configured in a vertical compressed configuration, a rolled compressed configuration, or a folded compressed configuration.

In another preferred embodiment of the invention, there is provided a valve wherein the annular support frame has a lower body portion and an upper collar portion, wherein the lower body portion in an expanded configuration forms a shape selected from a funnel, cylinder, flat cone, or circular hyperboloid.

In another preferred embodiment of the invention, there is provided a valve wherein said annular support frame is comprised of a braided, wire, or laser-cut wire frame, and said annular support frame is covered with a biocompatible material.

In another preferred embodiment of the invention, there is provided a valve wherein the annular support frame has a side profile of a flat cone shape having a diameter R of 40-80 mm, a diameter r of 20-60 mm, and a height of 5-60 mm.

In another preferred embodiment of the invention, there is provided a valve wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In another preferred embodiment of the invention, there is provided a valve wherein the annular support frame has a side profile of an hourglass shape having a top diameter R1 of 40-80 mm, a bottom diameter R2 of 50-70 mm, an internal diameter r of 20-60 mm, and a height of 5-60 mm.

In another preferred embodiment of the invention, there is provided a valve wherein the valve in an expanded configuration has a central vertical axis that is substantially parallel to the first direction.

In another preferred embodiment of the invention, there is provided a valve wherein the flow control component has an internal diameter of 20-60 mm and a height of 10-40 mm, and a plurality of leaflets of pericardial material joined to form a rounded cylinder at an inflow end and having a flat closable aperture at an outflow end.

In another preferred embodiment of the invention, there is provided a valve wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

In another preferred embodiment of the invention, there is provided a valve wherein the distal anchoring tab is comprised of wire loop, a wire frame, a laser cut frame, an integrated frame section, or a stent, and the distal anchoring tab extends from about 10-40 mm away from the distal side of the annular support frame.

In another preferred embodiment of the invention, there is provided a valve wherein the proximal anchoring tab is comprised of wire loop, a wire frame, a laser cut frame, an integrated frame section, or a stent, and the distal anchoring tab extends from about 10-40 mm away from the proximal side of the annular support frame.

In another preferred embodiment of the invention, there is provided a valve, further comprising an upper distal anchoring tab attached to a distal upper edge of the annular support frame, the upper distal anchoring tab comprised of wire loop, a wire frame, a laser cut frame, an integrated frame section, or a stent, and extends from about 2-20 mm away from the annular support frame.

In another preferred embodiment of the invention, there is provided a valve, comprising at least one tissue anchor connected to the annular support frame for engaging native tissue.

In another preferred embodiment of the invention, there is provided a valve, wherein the outer perimeter wall comprises a front wall portion that is a first flat panel and a back wall portion that is a second flat panel, and wherein a proximal fold area and a distal fold area each comprise a sewn seam, a fabric panel, a rigid hinge, or a flexible fabric span without any wire cells.

In another preferred embodiment of the invention, there is provided a valve, wherein the annular support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

Process for Manufacturing

In another preferred embodiment of the invention, there is provided a process for manufacturing a side delivered transcatheter prosthetic heart valve frame, comprising:

(i) using additive or subtractive metal or metal-alloy manufacturing to produce a self-expanding annular support frame, said annular support frame having a central channel and an outer perimeter wall circumscribing a central vertical axis in an expanded configuration, said annular support frame having a distal side and a proximal side, a flow control component mounted within the annular support frame and configured to permit blood flow in a first direction through an inflow end of the valve and block blood flow in a second direction, opposite the first direction, through an outflow end of the valve, a distal anchoring tab mounted on the distal side of the annular support frame, a proximal anchoring tab mounted on the proximal side of the annular support frame, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a length-wise cylindrical axis of the delivery catheter, wherein the valve has a height of about 5-60 mm and a diameter of about 25-80 mm, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining.

In another preferred embodiment of the invention, there is provided a process of manufacturing further comprising the steps of: (ii) mounting a flow control component within the valve frame, said flow control component configured to permit blood flow along the central vertical axis through an inflow end of the flow control component and block blood flow through an outflow end of the valve, and (iii) covering an outer surface of the valve frame with a pericardium material or similar biocompatible material.

Method of Compressing

In another preferred embodiment of the invention, there is provided a method for compressing an implantable prosthetic heart valve for length-wise orthogonal release of the valve from a delivery catheter, comprising the steps: flattening, rolling or folding the implantable prosthetic heart valve into a compressed configuration wherein the long-axis of the compressed configuration of the valve is substantially parallel to a length-wise cylindrical axis of the delivery catheter, wherein the implantable prosthetic heart valve comprises an annular support frame having a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, a proximal anchoring tab mounted on a proximal side of the annular support frame, wherein the valve has a height of about 5-60 mm and a diameter of about 25-80 mm.

In another preferred embodiment of the invention, there is provided a method of compressing, wherein the implantable prosthetic heart valve is rolled or folded into a compressed configuration using a step selected from the group consisting of: (i) unilaterally rolling into a compressed configuration from one side of the annular support frame; (ii) bilaterally rolling into a compressed configuration from two opposing sides of the annular support frame; (iii) flattening the annular support frame into two parallel panels that are substantially parallel to the long-axis, and then rolling the flattened annular support frame into a compressed configuration; and (iv) flattening the annular support frame along a vertical axis to reduce a vertical dimension of the valve from top to bottom.

Method for Delivery

In another preferred embodiment of the invention, there is provided a method for orthogonal delivery of implantable prosthetic heart valve in the body, the method comprising the steps: (i) advancing a distal end of a guide wire to a distal location, wherein the distal location is a pulmonary artery or a left ventricle of a heart, wherein the guide wire starts outside of a patient using femoral vein access or brachiocephalic vein access, and extends through an inferior vena cava or a superior vena cava to a right atrium, and extends from the right atrium through the tricuspid valve to the pulmonary artery or extends from the right atrium across the atrial septum in a transeptal access through the mitral valve and into a left ventricle; (ii) advancing a delivery catheter over the guide wire to a target location, where the target location is a right atrium of the tricuspid valve or a left atrium of the mitral valve; (iii) advancing and delivering an orthogonally compressed self-expandable prosthetic heart valve to the target location in the body, wherein a compressed configuration of the valve has a long-axis substantially parallel to a length-wise cylindrical axis of the delivery catheter, wherein the expanded configuration of the valve has a height of about 5-60 mm and a diameter of about 25-80 mm, wherein the valve comprises an annular support frame having a flow control component mounted within the annular support frame and configured to permit blood flow in a first direction through an inflow end of the valve and block blood flow in a second direction, opposite the first direction, through an outflow end of the valve, a distal anchoring tab is mounted on a distal side of the annular support frame, the distal anchoring tab having a length of 10-40 mm and a width of 2-10 mm, wherein the guide wire is threaded through a threading aperture on or within the distal anchoring tab, at least one proximal anchoring tab is mounted on a proximal side of the annular support frame, the proximal anchoring tab having a length of 2-25 mm and a width of 2-10 mm, and a valve advancing tool comprising an elongated sheath wherein the guide wire is within a lumen of the sheath, wherein the outer diameter of the sheath is larger than the inner diameter of the threading aperture on the distal anchoring tab, wherein when the sheath is advanced over the guide wire in a distal direction, and a distal end of the sheath contacts a proximal surface of the threading aperture, the valve is advanced distally through the delivery catheter by the distally-directed pulling force that the sheath imparts to the distal anchoring tab; (iv) partially releasing the valve from the delivery catheter by advancing the sheath over the guide wire, and positioning the distal anchoring tab at a desired anchoring area of the target location, wherein the desired anchoring area is selected from a right ventricular outflow tract (RVOT) of a right ventricle, and a sub-annular area below an A1-P1 antero-lateral commissure of a mitral valve, wherein positioning the distal anchoring tab holds the valve at a raised angle of at least 30 degrees to a localized annular plane relative to the horizontal axis of the valve and the delivery catheter, wherein partially releasing the valve permits blood to flow partially around the prosthetic valve and through the native leaflets, and partially through the flow control component of the prosthetic valve to provide a gradual blood flow transition from flow through native leaflets to complete flow through the prosthetic valve; (v) completing release of the entire valve from the delivery catheter by advancing the sheath over the guide wire, seating the valve in the native annulus by applying a downward force in the direction of the ventricle; and (vi) seating the at least one proximal anchoring tab at a second desired anchoring area.

In another preferred embodiment of the invention, there is provided a method for orthogonal delivery of implantable prosthetic heart valve to a desired location in the body, the method comprising the steps: advancing a delivery catheter to the desired location in the body and delivering an expandable prosthetic heart valve to the desired location in the body by releasing the valve from the delivery catheter, wherein the valve comprises an annular support frame having a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, and a proximal anchoring tab mounted on a proximal side of the annular support frame, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the compressed configuration, wherein the valve has a height of about 5-60 mm and a diameter of about 25-80 mm.

In another preferred embodiment of the invention, there is provided a method of delivery, wherein releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In another preferred embodiment of the invention, there is provided a method of delivery, comprising the additional step of anchoring one or more tissue anchors attached to the valve into native tissue.

In another preferred embodiment of the invention, there is provided a method of delivery, comprising the additional step of positioning the distal anchoring tab of the heart valve prosthesis into the right ventricular outflow tract of the right ventricle.

In another preferred embodiment of the invention, there is provided a method of delivery, comprising the additional steps of positioning the distal anchoring tab of the heart valve prosthesis into the right ventricular outflow tract of the right ventricle, and positioning an upper distal anchoring tab into a supra-annular position, and the upper distal anchoring tab providing a supra-annular downward force in the direction of the ventricle and distal anchoring tab providing a sub-annular upward force in the direction of the atrium.

In another preferred embodiment of the invention, there is provided a method of delivery, comprising the additional step of rotating the heart valve prosthesis using a steerable catheter along an axis parallel to the plane of the valve annulus.

Method for Loading

In another preferred embodiment of the invention, there is provided a method for orthogonally loading an implantable prosthetic heart valve into a delivery catheter, the method comprising the steps: loading an implantable prosthetic heart valve into a tapering fixture or funnel attached to a delivery catheter, wherein the valve comprises a annular support frame having a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, and a proximal anchoring tab mounted on a proximal side of the annular support frame, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

In another preferred embodiment of the invention, there is provided a method for loading, wherein the step of loading includes attaching a loading accessory to a valve sidewall, to a valve cuff, to the distal anchoring tab, to the proximal anchoring tab, or a combination thereof, wherein the loading accessory is pushing rod or a pulling wire, and wherein the tapering fixture or funnel has a compression element on an inner surface of the tapering fixture or funnel to facilitate compression, iris-ing, or spiraling of the uncompressed valve.

Method for Improving Flow

In another preferred embodiment of the invention, there is provided a method for improving hemodynamic flow during implantation of a transcatheter prosthetic heart valve, comprising: advancing a delivery catheter to the desired location in the body and delivering the valve of claim 1 to the desired location in the body; partially releasing the valve from the delivery catheter to establish blood flow around the partially released valve and establish blood flow through the flow control component; completely releasing the valve from the delivery catheter while maintaining attachment to the valve with a positioning catheter or wire to transition to increased blood flow through the flow control component and decreasing blood flow around the valve; and deploying the valve into a final mounted position to transition to complete blood flow through the flow control component and minimal or no blood flow around the valve, and disconnecting and withdrawing the positioning catheter or wire from the valve.

In another preferred embodiment of the invention, there is provided a method for improving flow, wherein the distal anchoring tab is an RVOT tab positioned in the RVOT during the transition from partial release of the valve to complete release of the valve.

BRIEF DESCRIPTION OF THE SEVERAL VIEWS OF DRAWING

Figure 9:
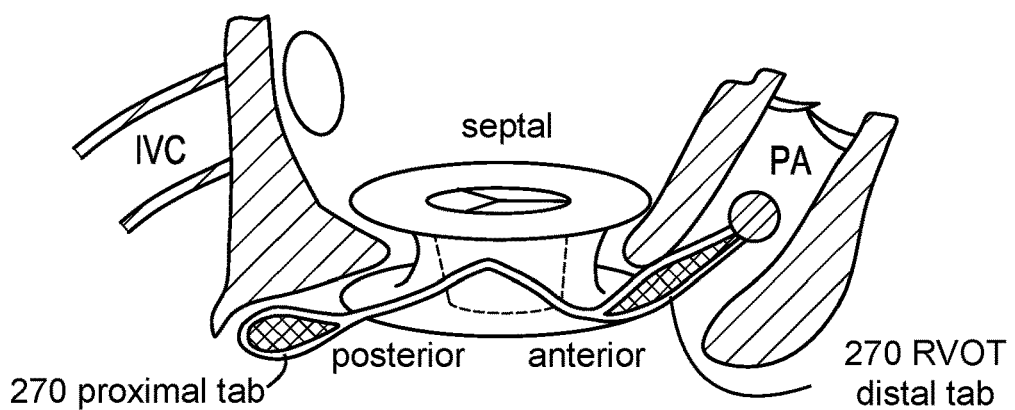

FIG. 9 is an illustration of a ANTERIOR SIDE PERSPECTIVE view of a side delivered valve seated with the native tricuspid annulus with collar portion laying atrially above the tricuspid annulus and leaflets, lower body portion extending into and through the annulus to provide corrective hemodynamic flow from the flow control component, and distal RVOT footer anchoring tab, proximal anchoring tab, and tension arm extender wire connecting the distal tab and the proximal tab.

Figure 10:
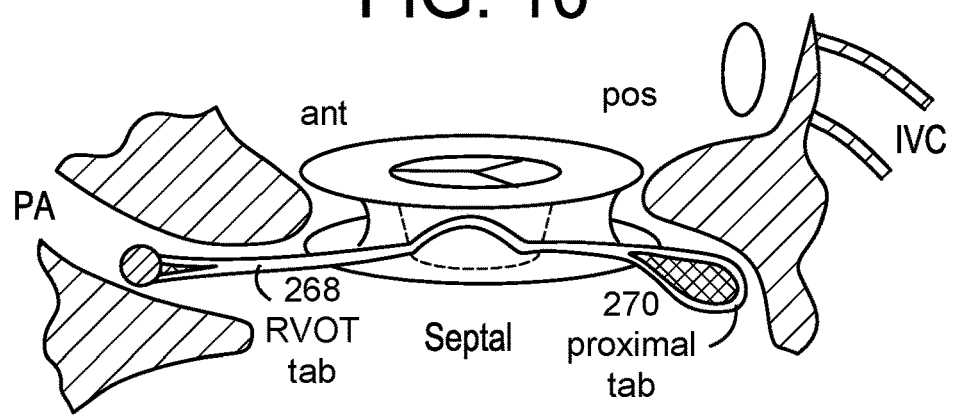

FIG. 10 is an illustration of a SEPTAL SIDE PERSPECTIVE view of a side delivered valve seated with the native tricuspid annulus with collar portion laying atrially above the tricuspid annulus and leaflets, lower body portion extending into and through the annulus to provide corrective hemodynamic flow from the flow control component, and distal RVOT footer anchoring tab, proximal anchoring tab, and tension arm extender wire connecting the distal tab and the proximal tab.

Figure 11:
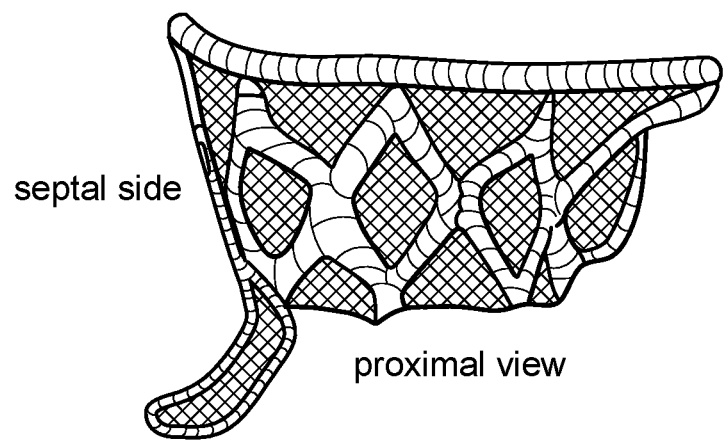

FIG. 11 is an illustration of a PROXIMAL SIDE VIEW of the valve with proximal tab extending toward the viewer out of the page.

Figure 12:
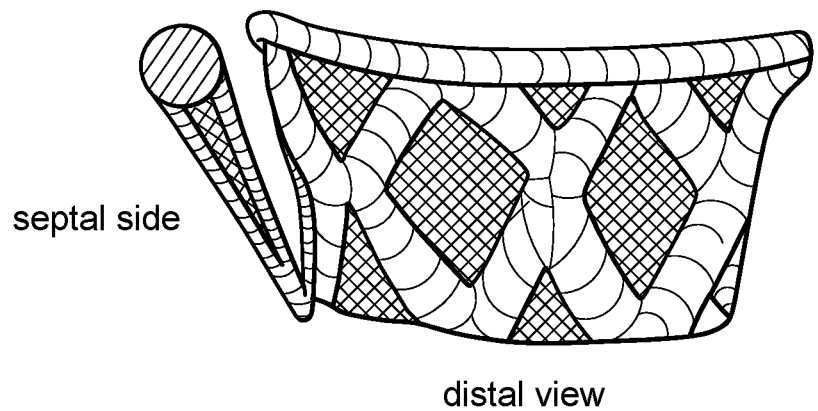

FIG. 12 is an illustration of a DISTAL SIDE VIEW of the valve with distal tab extending toward the viewer out of the page.

Figure 13:
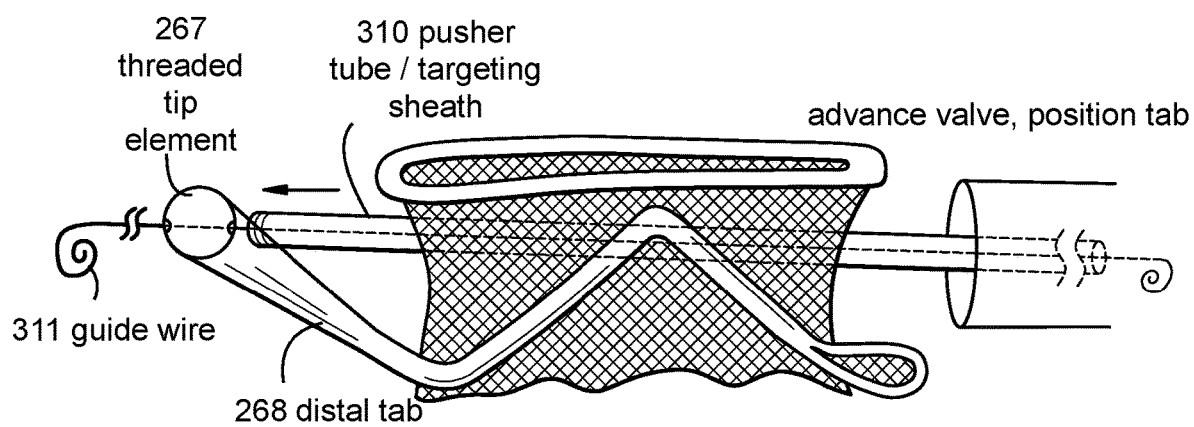
Figure 14:
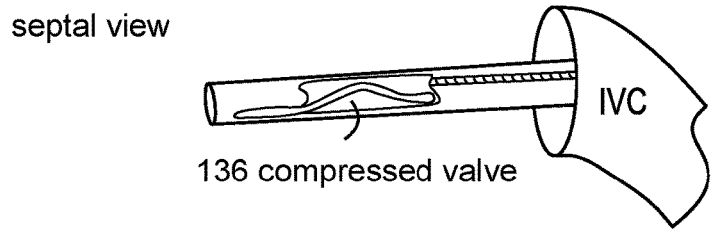
Figure 15:
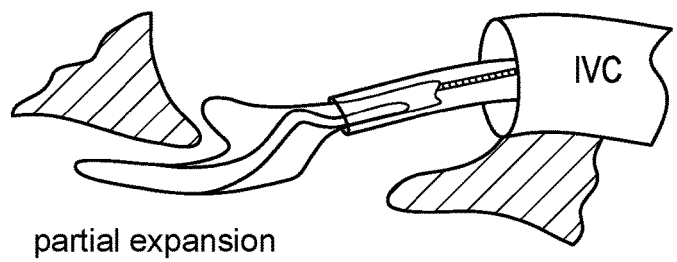
Figure 16:
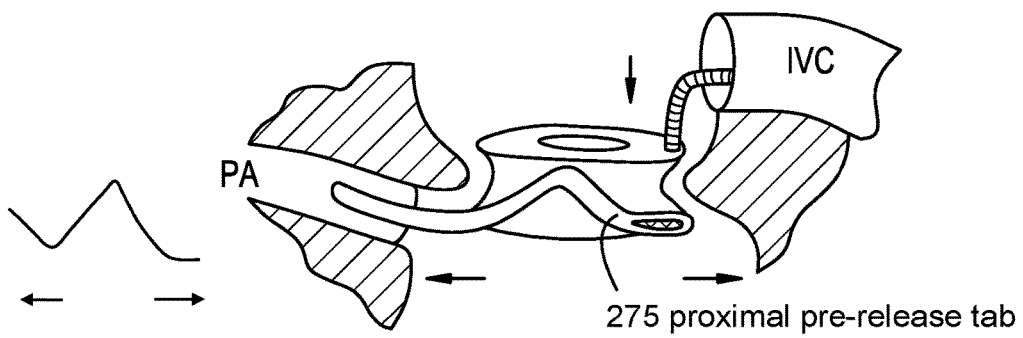
Figure 17:
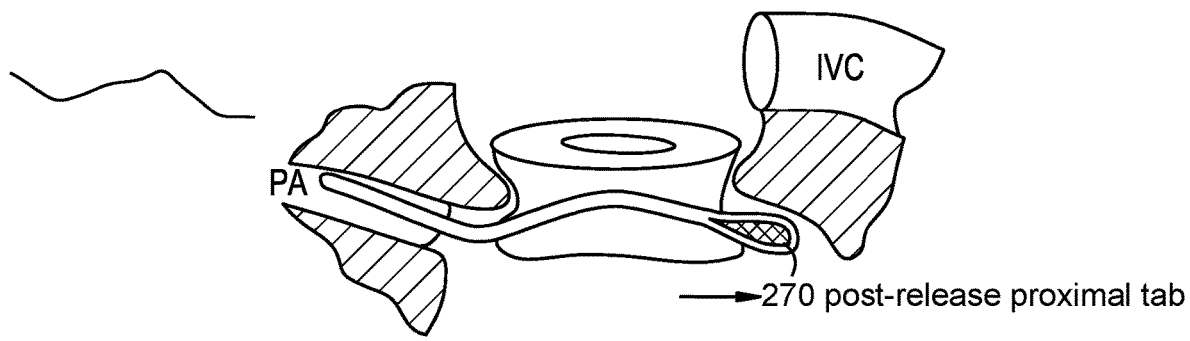
Figure 18:
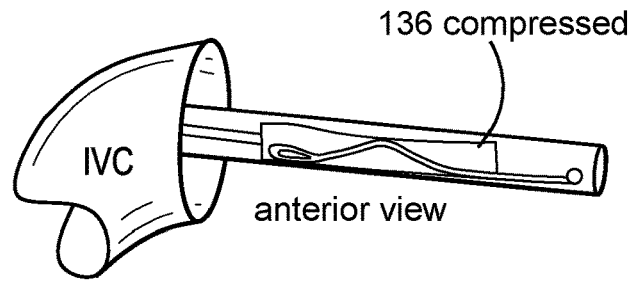
Figure 19:
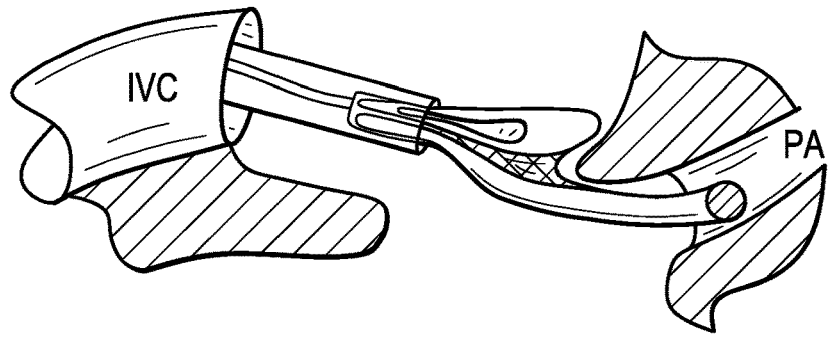
Figure 20:
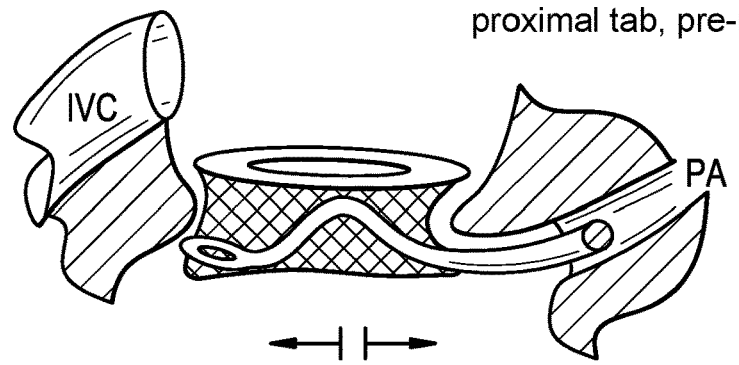
Figure 21:
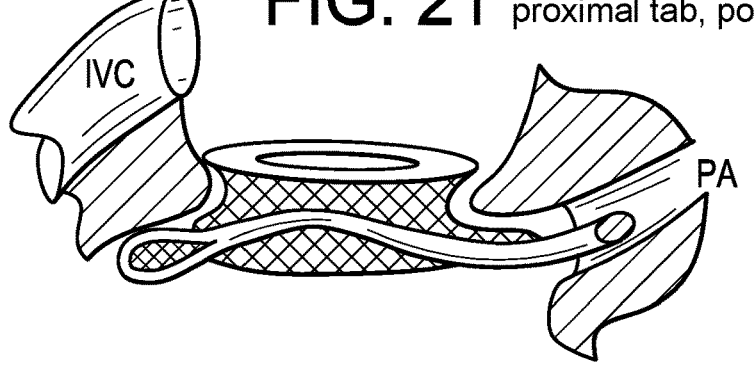
Figure 22:
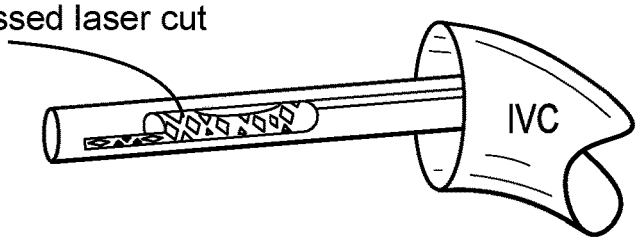
Figure 23:
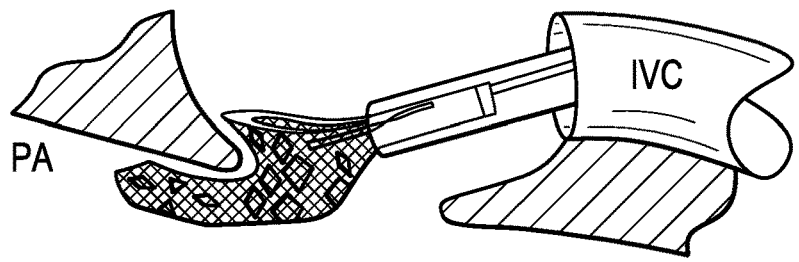
Figure 24:
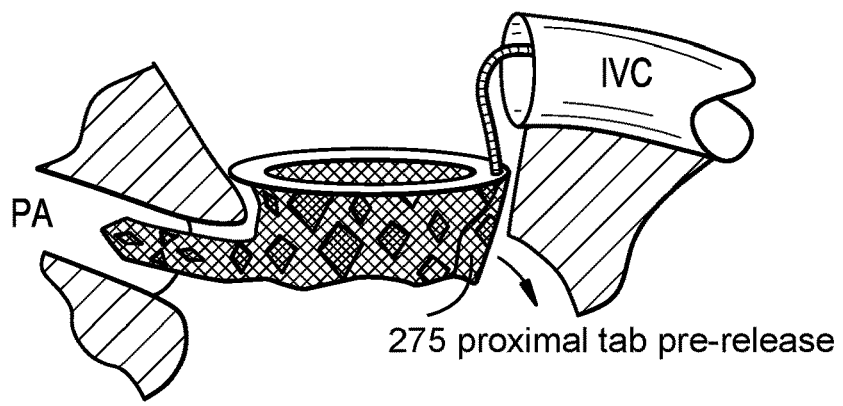
Figure 25:
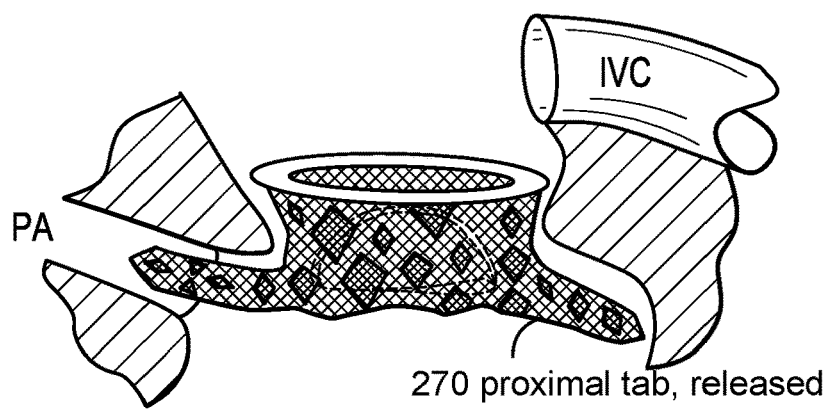
Figure 26:
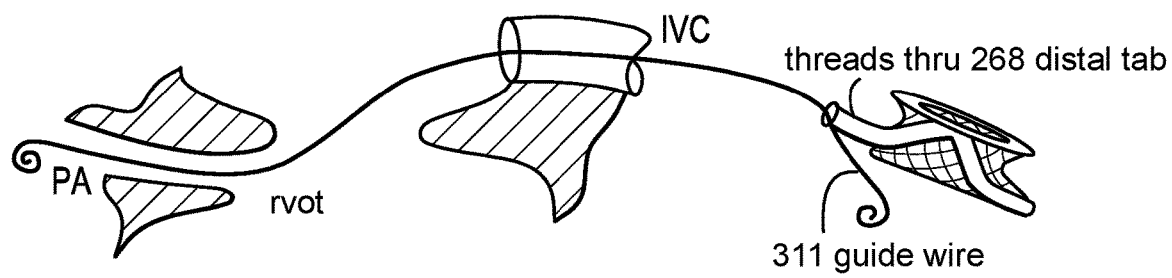
Figure 27:
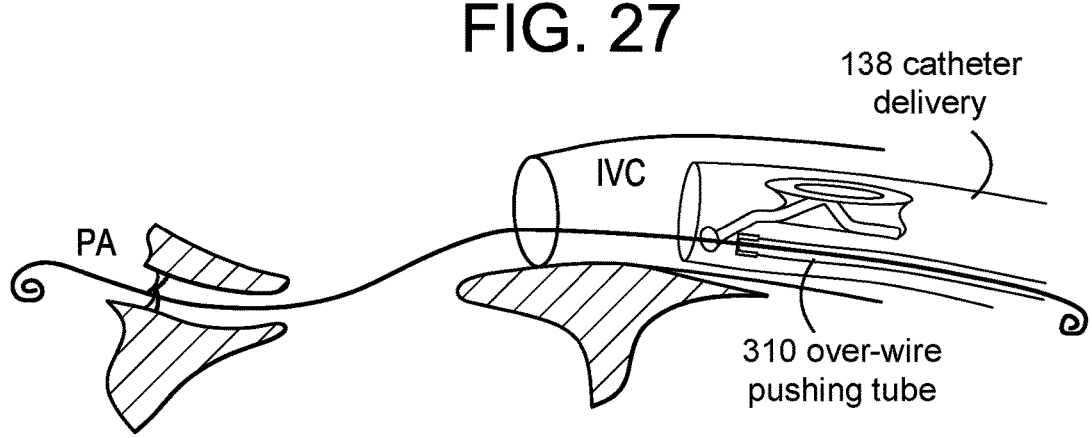
Figure 28:
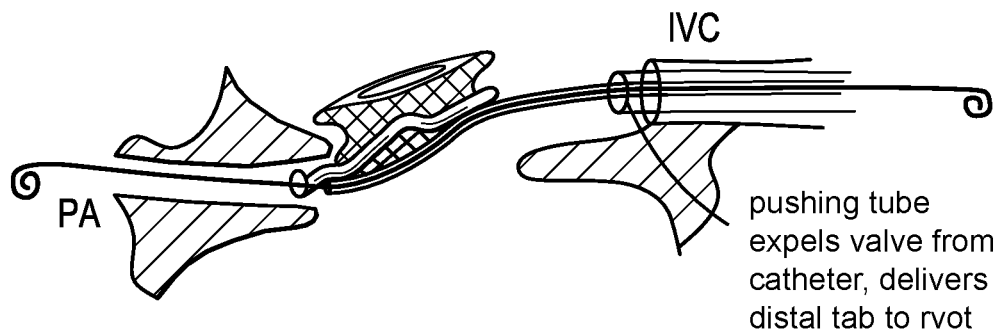
Figure 29:
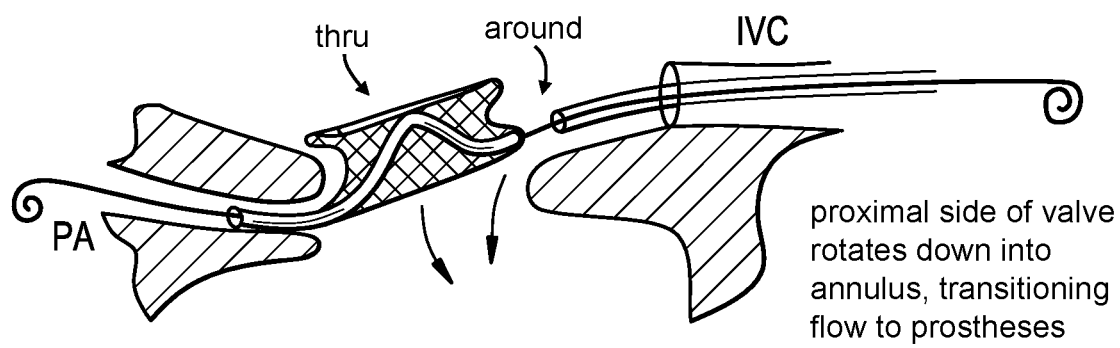
Figure 30:
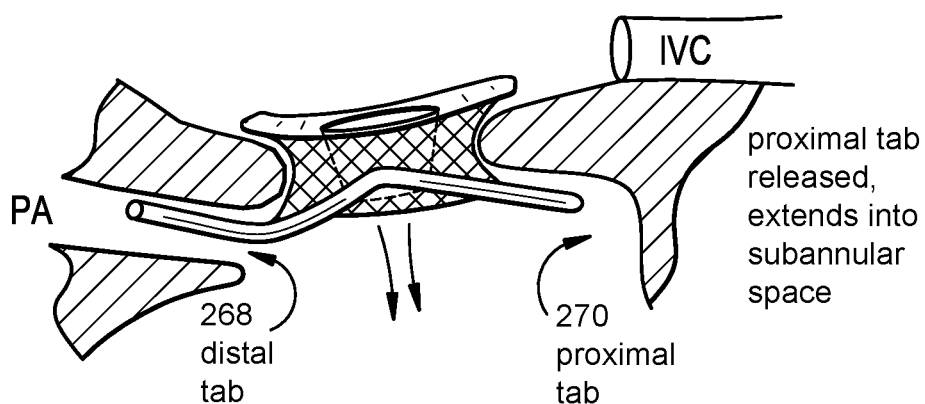

FIG. 13 is an illustration of a SIDE VIEW of a valve according to the invention with a guide wire threading through a distal tab tip element, and a pusher tube extending from a delivery catheter, the pusher tube sheathed over the guide wire but unable to pass the tip element thereby providing a mechanism for pulling the valve out of the delivery catheter from the distal side to avoid damaging compressive pushing forces that usually attend the expelling process of a standard prosthetic valve from a delivery catheter.

FIGS. 14-15-16-17 are illustrations of a SEPTAL SIDE VIEW of a process whereby a compressed valve is delivered via catheter, the compressed valve is partially ejected and allowed to partially self-expand to establish blood flow around and through the valve, the valve is then seated into the native annulus, and finally the proximal tab is detached from its securement mechanism and the proximal tab and the distal tab provide sub-annular anchoring.

FIGS. 18-19-20-21 are illustrations of an ANTERIOR SIDE VIEW of a process whereby a compressed valve is delivered via catheter, the compressed valve is partially ejected and allowed to partially self-expand to establish blood flow around and through the valve, the valve is then seated into the native annulus, and finally the proximal tab is detached from its securement mechanism and the proximal tab and the distal tab provide sub-annular anchoring.

FIGS. 22-23-24-25 are illustrations of a SEPTAL SIDE VIEW of a process whereby a compressed laser cut valve is delivered via catheter, the compressed valve is partially ejected and allowed to partially self-expand to establish blood flow around and through the valve, the valve is then seated into the native annulus, and finally the proximal tab is detached from its securement mechanism and the proximal tab and the distal tab provide sub-annular anchoring.

FIGS. 26-27-28-29-30 are illustrations of a SEPTAL SIDE VIEW of a process whereby a guide wire is initially deployed into the pulmonary artery, the compressed valve is delivered via catheter, the compressed valve is partially ejected and allowed to partially self-expand to establish blood flow around and through the valve, the valve is then seated into the native annulus, and finally the proximal tab is detached from its securement mechanism and the proximal tab and the distal tab provide sub-annular anchoring.

Figure 31:
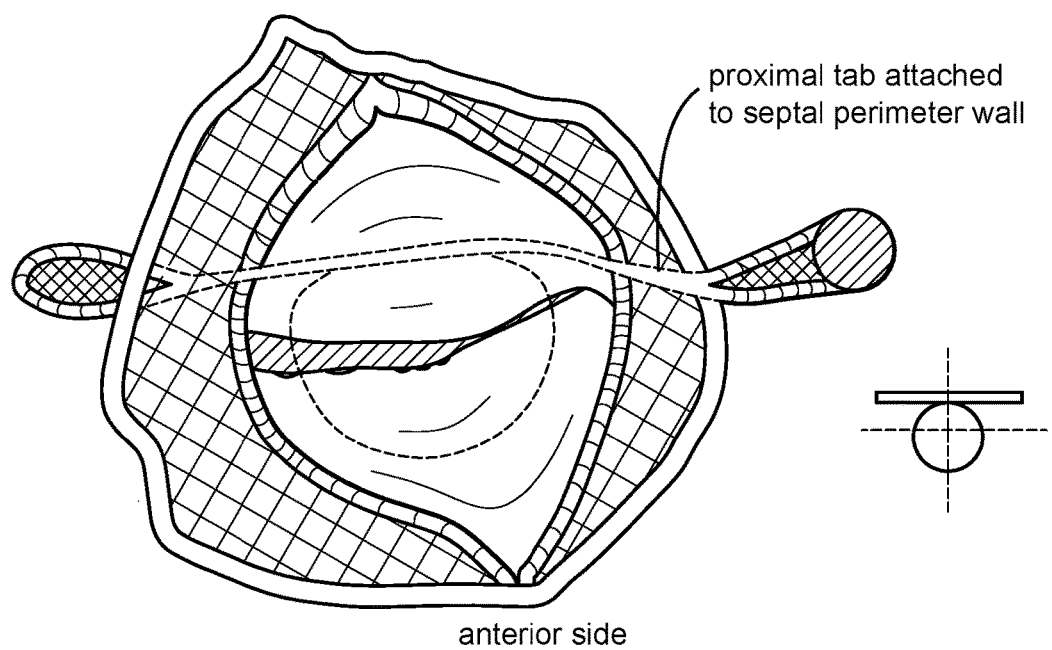

FIG. 31 is an illustration of a TOP ANTERIOR VIEW of a valve according to the present invention with the dual tab mechanism (distal and proximal) attached around the circumference of the body portion of the valve, beneath the collar portion.

Figure 32:
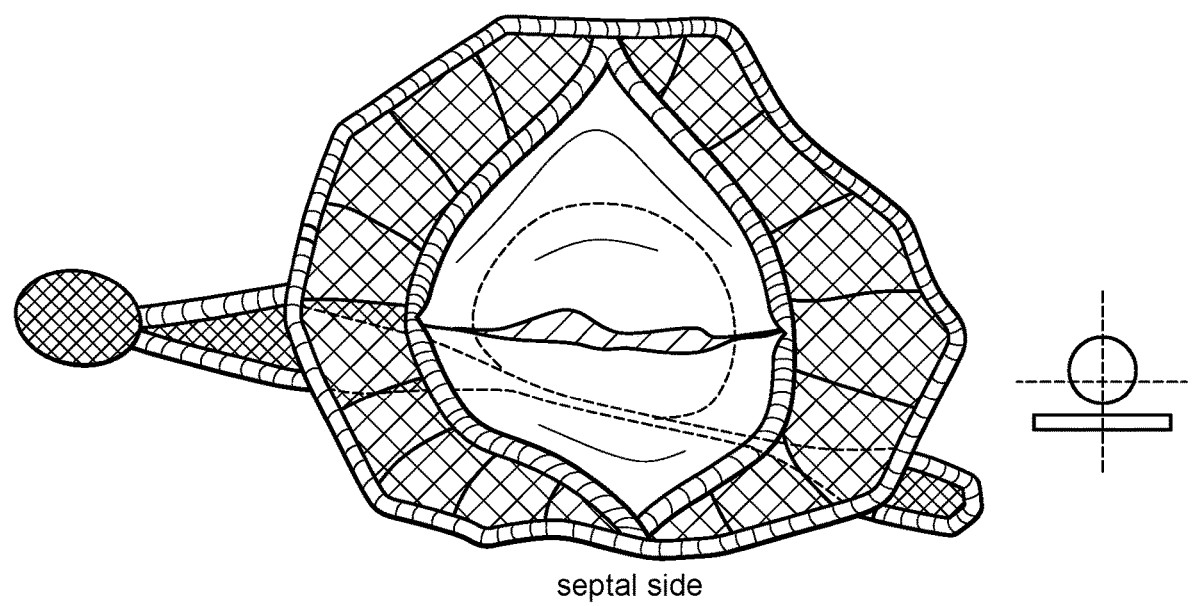

FIG. 32 is an illustration of a TOP SEPTAL VIEW of a valve according to the present invention with the dual tab mechanism (distal and proximal) attached around the circumference of the body portion of the valve, beneath the collar portion.

Figure 33:
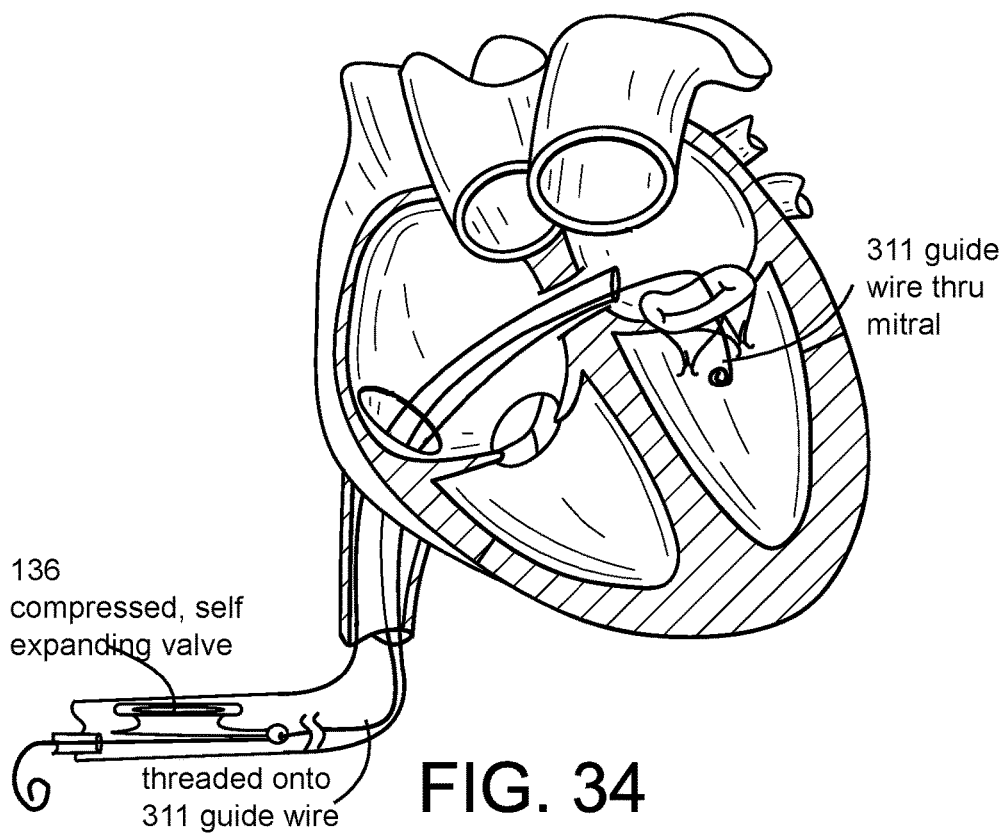

FIG. 33 is an illustration of a SIDE VIEW of a heart with a delivery catheter having a compressed valve where a distal tab element is threaded onto the guide wire leading up the femoral vein through the IVC, a pusher or valve advancing tool is a sheath on the guide wire, and the system is ready to be delivered to the left atrium.

Figure 34:
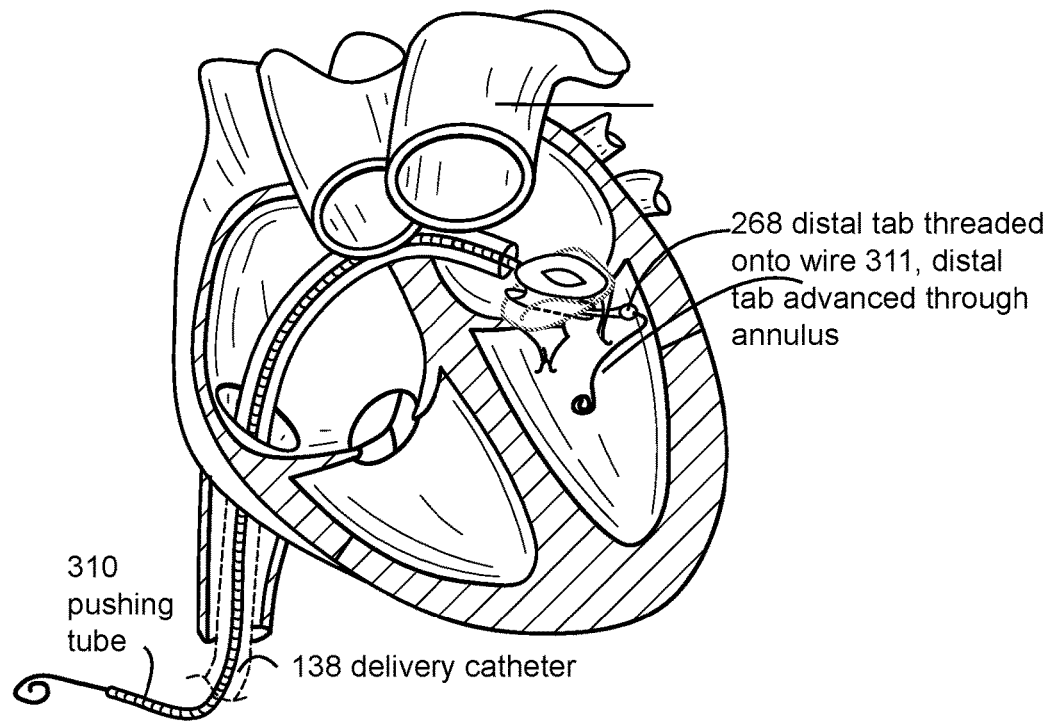

FIG. 34 is an illustration of a SIDE VIEW of a heart having a delivery catheter advanced transeptally to the left atrium from the femoral/IVC access, and valve advancing tool is positioning the distal tab in the sub-annular mitral antero-lateral commissure anchoring area.

FIG. 35 is an illustration of a SIDE VIEW of a heart having a side delivered mitral valve prosthesis according to the present invention, with the transeptal stitch closing the access point.

FIG. 36 is an illustration of a TOP VIEW a side delivered valve positioned relative to the native mitral annulus and shows how distal tab and proximal tab provide anchoring in the A1-P1 and A3-P3 commissural anchoring areas.

FIG. 37 is an illustration of a TOP VIEW of a native valve annulus in solid line with a prosthetic valve in dashed line.

Figure 38:
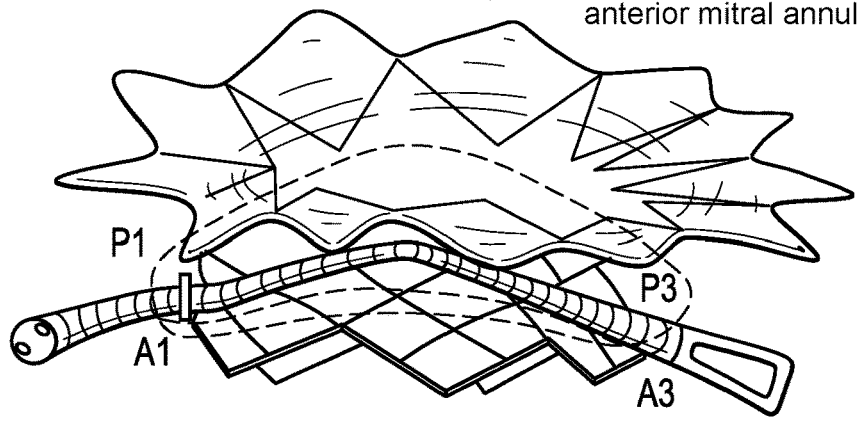
Figure 39:
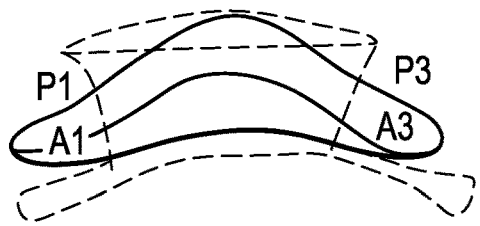
Figure 40:
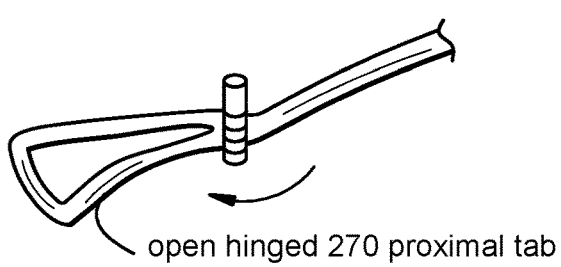
Figure 42:
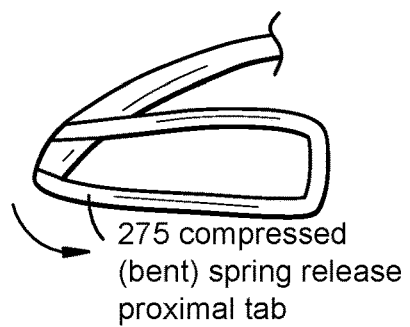
Figure 41:
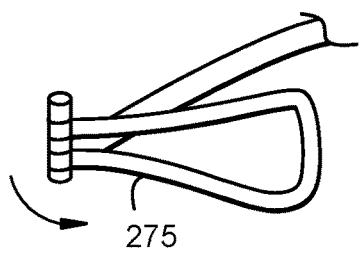
Figure 43:
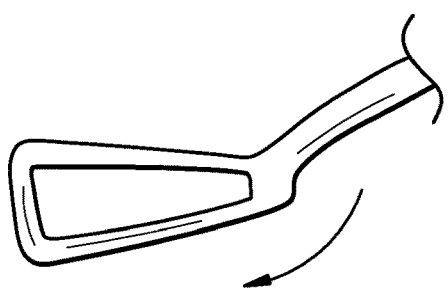

FIG. 38 is an illustration of a SIDE VIEW from the anterior side of the mitral annulus of a side delivered valve positioned relative to the native mitral annulus and shows how distal tab and proximal tab provide anchoring in the A1-P1 and A3-P3 commissural anchoring FIG. 39 is an illustration of a SIDE VIEW of a native valve annulus in solid line with a prosthetic valve in dashed line.

FIG. 40-41-42-43 are illustrations of a proximal tab fold and release mechanism, either using a mechanicla hinge or similar mechanism, or using the spring aspect of the superelastic material.

FIG. 44 is an illustration of a TOP VIEW a side delivered valve positioned relative to the native tricuspid annulus and shows how distal tab and proximal tab provide anchoring in the distal (RVOT) and proximal (adjacent IVC) anchoring areas.

FIG. 45 is an illustration of a TOP VIEW of a native valve annulus in solid line with a prosthetic valve in dashed line.

FIG. 46 is an illustration of a SIDE PERSPECTIVE VIEW of a valve having multiple, e.g. 3 or more, sub-annular anchoring tabs.

FIG. 47 is a text flow chart showing process steps of one preferred method of delivery of an orthogonally compressed, delivered, transitioned, and released prosthetic valve.

DETAILED DESCRIPTION OF THE INVENTION

The invention is directed to a dual-tab transcatheter heart valve replacement that is a low profile, side delivered implantable prosthetic heart valve having an ring-shaped or annular support frame, an inner 2- or 3-panel sleeve, an elongated sub-annular distal anchoring tab extending into the right ventricular outflow tract, an elongated sub-annular proximal anchoring tab extending into the proximal sub-annular space, preferably between the anterior and the posterior leaflets.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Side-Delivery or Orthogonal Delivery

In the description and claims herein, the terms "side-delivered", "side-delivery", "orthogonal", "orthogonally delivered" and so forth are used to describe that the valves of the present invention are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Traditional valves have a central cylinder axis that is parallel to the length-wise axis of the delivery catheter and are deployed from the end of the delivery catheter and expanded radially outward from the central annular axis, in a manner akin to pushing a closed spring-loaded umbrella out of a sleeve to make it spring open. However, the valves of the present invention are compressed and delivered in a sideways manner. To begin with the shape of the expanded valve is that of a large diameter shortened cylinder with an extended collar or cuff. The valves are compressed, in one preferred embodiment, where the central axis of the valve is roughly perpendicular to (orthogonal to) the length-wise axis of the delivery catheter. In one preferred embodiment, the valves are compressed vertically, similar to collapsing the height of a cylinder accordion-style from taller to shorter, and the valves are also compressed by folding a front panel against a back panel. In another preferred embodiment, the valves may be compressed by rolling.

Traditional valves can only be expanded as large as what the internal diameter of the delivery catheter will allow.

Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, eg. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with trans-luminal and is functionally related to the term "percutaneous" as it relates to delivery of heart valves.

In preferred embodiments of the invention, the transcatheter approach includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g. fossa ovalis or lower, via the IVC-femoral or the SVC-jugular approach.

Annular Support Frame

In the description and claims herein, the term "annular support frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular support frame has a flow control component mounted within the annular support frame and configured to permit blood flow in a first direction through an inflow end of the valve and block blood flow in a second direction, opposite the first direction, through an outflow end of the valve.

Since the frame is preferably made of superelastic metal or alloy such as Nitinol, the frame is compressible. Preferably, the frame is constructed of a plurality of compressible wire cells having a orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both.

In one preferred embodiment, the annular support frame used in the prosthetic heart valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

In a preferred embodiment, the horizontal x-axis of the valve is orthogonal to (90 degrees), or substantially orthogonal to (75-105 degrees), or substantially oblique to (45-135 degrees) to the central vertical y-axis when in an expanded configuration.

In a preferred embodiment, the horizontal x-axis of the compressed configuration of the valve is substantially parallel to a length-wise cylindrical axis of the delivery catheter.

In another preferred embodiment, the valve has a compressed height (y-axis) and width (z-axis) of 6-15 mm, preferably 8-12 mm, and more preferably 9-10 mm, and an expanded deployed height of about 5-60 mm, preferably about 5-30 mm, and more preferably about 5-20 mm or even 8-12 mm or 8-10 mm. It is contemplated in preferred embodiments that the length of the valve, x-axis, does not require compression since it can extend along the length of the central cylindrical axis of the delivery catheter.

In a preferred embodiment, the valve has an expanded diameter length and width of 25-80 mm, preferably 40-80 mm, and in certain embodiments length and/or width may vary and include lengths of 25 mm, 30 mm, 35 mm, 40 mm, 45 mm, 50 mm, 55 mm, 60 mm, 65 mm, 70 mm, 75 mm, and 80 mm, in combination with widths that are the same or different as the length.

In certain preferred embodiments, the valve is centric, or radially symmetrical. In other preferred embodiments, the valve is eccentric, or radially (y-axis) asymmetrical. In some eccentric embodiments, the outer frame may have a D-shape (viewed from the top) so the flat portion can be matched to the mitral annulus near the anterior leaflet.

In certain preferred embodiments, the inner frame holding the leaflet tissue is 25-29 mm in diameter, the outer frame is 50-70 mm in diameter, and the collar structure extends beyond the top edge of the outer frame by 10-30 mm to provide a seal on the atrial floor against perivalvular leaks (PVLs).

The atrial collar is shaped to conform to the native deployment location. In a mitral replacement, the atrial collar will be configured with varying portions to conform to the native valve. In one preferred embodiment, the collar will have a distal and proximal upper collar portion. The distal collar portion can be larger than the proximal upper collar portion to account for annular or subannular geometries.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of—, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers—

The tethers are made from surgical-grade materials such as Biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tine—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic heart valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene—glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

EXAMPLE

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In a preferred embodiment the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example—Manufacturing Process

In a preferred embodiment the invention includes a process for manufacturing a side delivered transcatheter prosthetic heart valve frame, comprising:
(i) using additive or subtractive metal or metal-alloy manufacturing to produce
a self-expanding annular support frame,
wherein the additive metal or metal-alloy manufacturing is 3D printing or direct metal laser sintering (powder melt), and
wherein the subtractive metal or metal-alloy manufacturing is photolithography, laser sintering/cutting, CNC machining, electrical discharge machining.

In another preferred embodiment, there is provided a process for manufacturing a side delivered transcatheter prosthetic heart valve frame, further comprising the steps of:
(ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Example—Compression Methods

In another preferred embodiment, there is provided a method of compressing, wherein the implantable prosthetic heart valve is rolled or folded into a compressed configuration using a step selected from the group consisting of:
(i) unilaterally rolling into a compressed configuration from one side of the annular support frame;
(ii) bilaterally rolling into a compressed configuration from two opposing sides of the annular support frame;
(iii) flattening the annular support frame into two parallel panels that are substantially parallel to the long-axis, and then rolling the flattened annular support frame into a compressed configuration; and
(iv) flattening the annular support frame along a vertical axis to reduce a vertical dimension of the valve from top to bottom.

DRAWINGS

Figure 1:
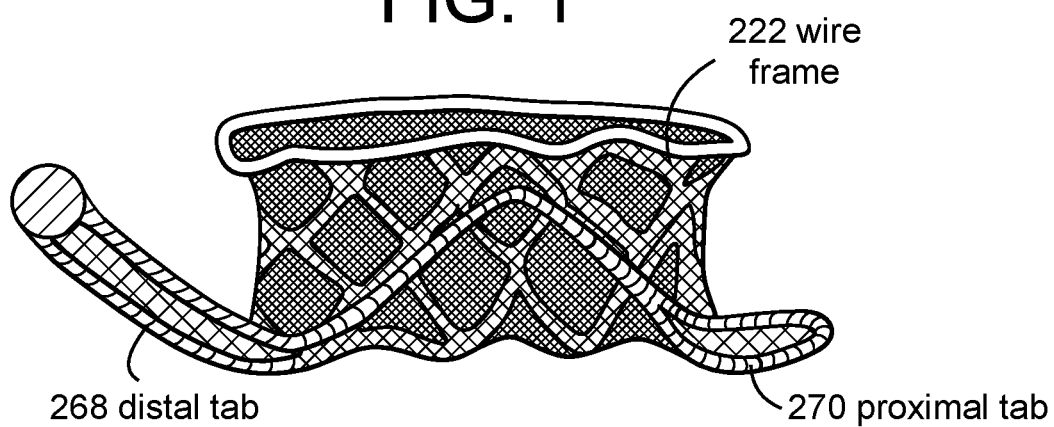
FIG. 1 is an illustration of a SIDE PERSPECTIVE view of a side delivered transcatheter heart valve with superelastic wire loop distal tab and a superelastic wire loop proximal tab according to the invention.

Referring now to the drawings, FIG. 1 is an illustration of a SIDE PERSPECTIVE view of a side delivered transcatheter heart valve 100 having wire frame 222 with superelastic wire loop distal tab 268 and a superelastic wire loop proximal tab 270 according to the invention.

Figure 2:
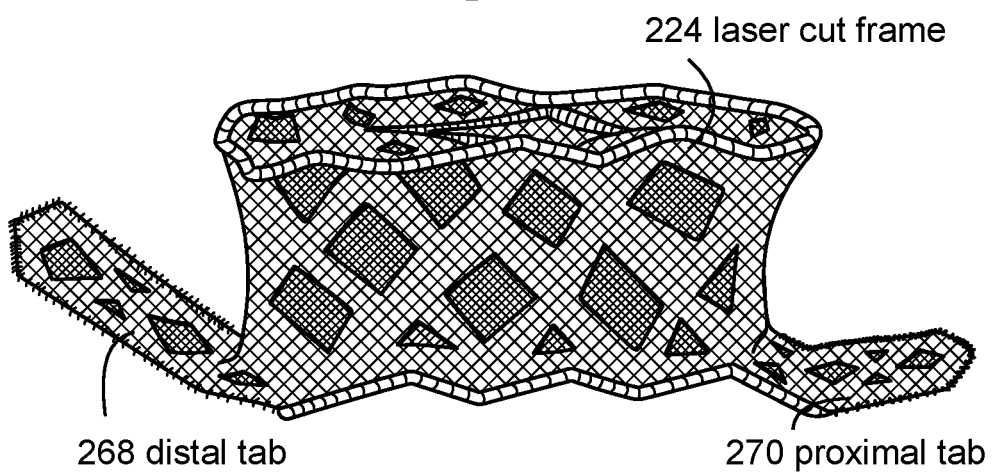
FIG. 2 is an illustration of a SIDE PERSPECTIVE view of a laser cut side delivered transcatheter heart valve with a laser cut distal tab and a laser cut proximal tab according to the invention.

FIG. 2 is an illustration of a SIDE PERSPECTIVE view of a laser cut frame 224 side delivered transcatheter heart valve 100 with a laser cut distal tab 268 and a laser cut proximal tab 270 according to the invention.

Figure 3:
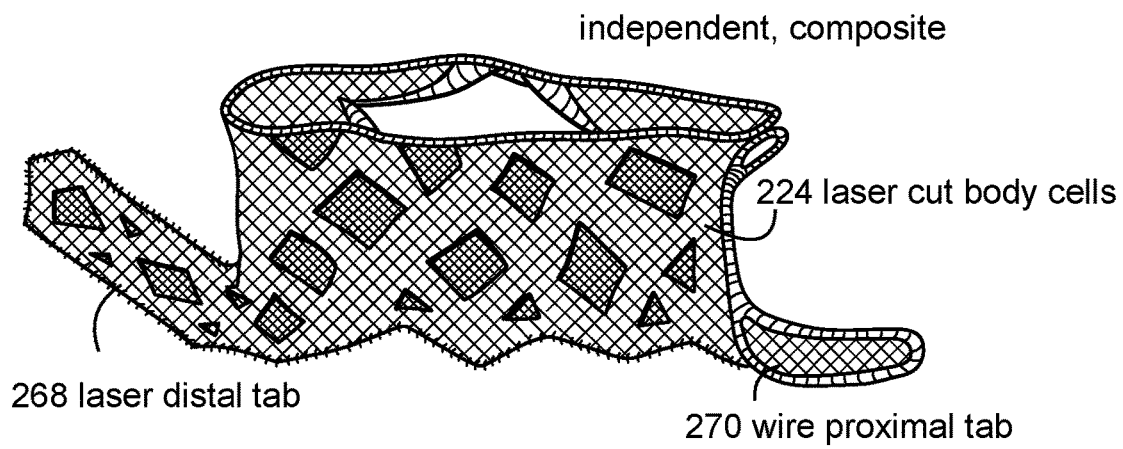
FIG. 3 is an illustration of a SIDE PERSPECTIVE view of a laser cut side delivered transcatheter heart valve with a laser cut distal tab and a wire loop proximal tab according to the invention.

FIG. 3 is an illustration of a SIDE PERSPECTIVE view of a laser cut framed 224 side delivered transcatheter heart valve 100 with a laser cut distal tab 268 and a wire loop proximal tab 270 according to the invention.

Figure 4:
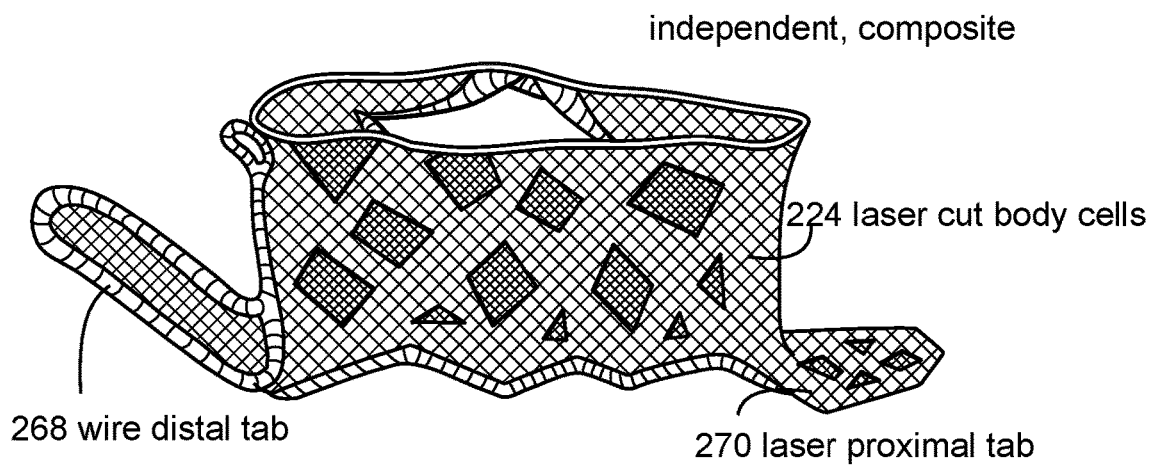
FIG. 4 is an illustration of a SIDE PERSPECTIVE view of a laser cut side delivered transcatheter heart valve with a superelastic wire loop distal tab and a laser cut proximal tab according to the invention.

FIG. 4 is an illustration of a SIDE PERSPECTIVE view of a laser cut framed 224 side delivered transcatheter heart valve 100 with a superelastic wire loop distal tab 268 and a laser cut proximal tab 270 according to the invention.

Figure 5:
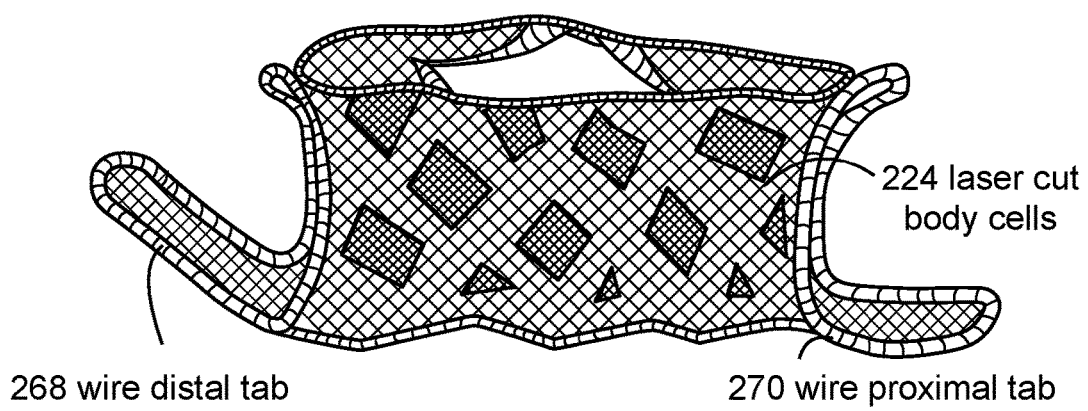
FIG. 5 is an illustration of a SIDE PERSPECTIVE view of a laser cut side delivered transcatheter heart valve with a superelastic wire loop distal tab and a superelastic wire loop proximal tab according to the invention.

FIG. 5 is an illustration of a SIDE PERSPECTIVE view of a laser cut framed 224 side delivered transcatheter heart valve with a superelastic wire loop distal tab 268 and a superelastic wire loop proximal tab 270 according to the invention.

Figure 6:
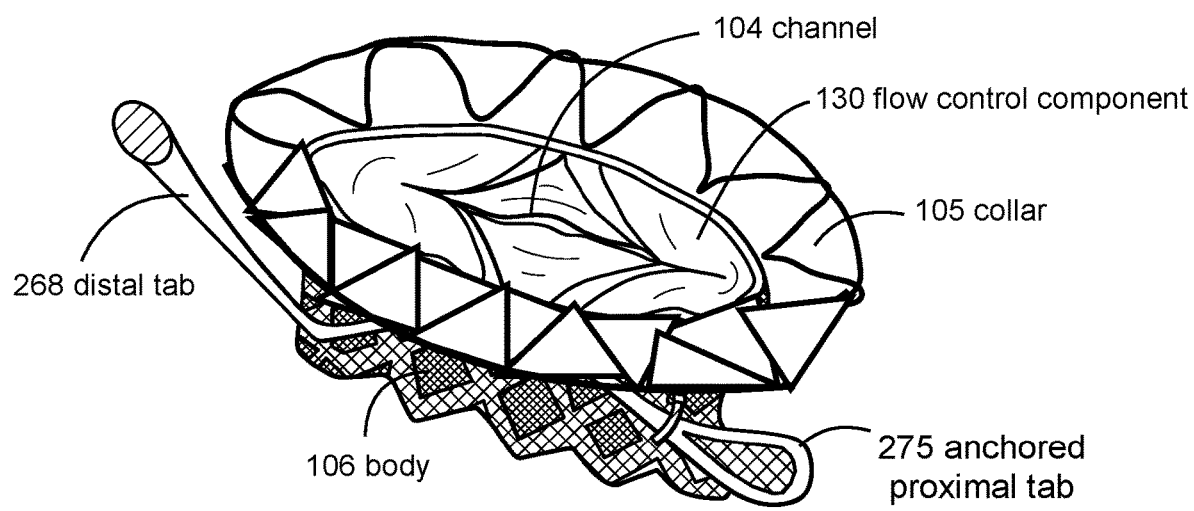
FIG. 6 is an illustration of a SIDE PERSPECTIVE view of a side delivered transcatheter heart valve with superelastic wire loop distal tab and a superelastic wire loop proximal tab in a pre-release, anchored configuration according to the invention.

FIG. 6 is an illustration of a SIDE PERSPECTIVE view of a side delivered transcatheter heart valve 100 with superelastic wire loop distal tab 268 and a superelastic wire loop proximal tab 270 in a pre-release, anchored configuration according to the invention. FIG. 6 shows outer wall/body 106 with atrial anchoring collar 105 disposed around a top edge. Flow control component 130 is disposed within the lumen of the cylindrical valve body 106 and defines the channel 104 for blood flow.

Figure 7:
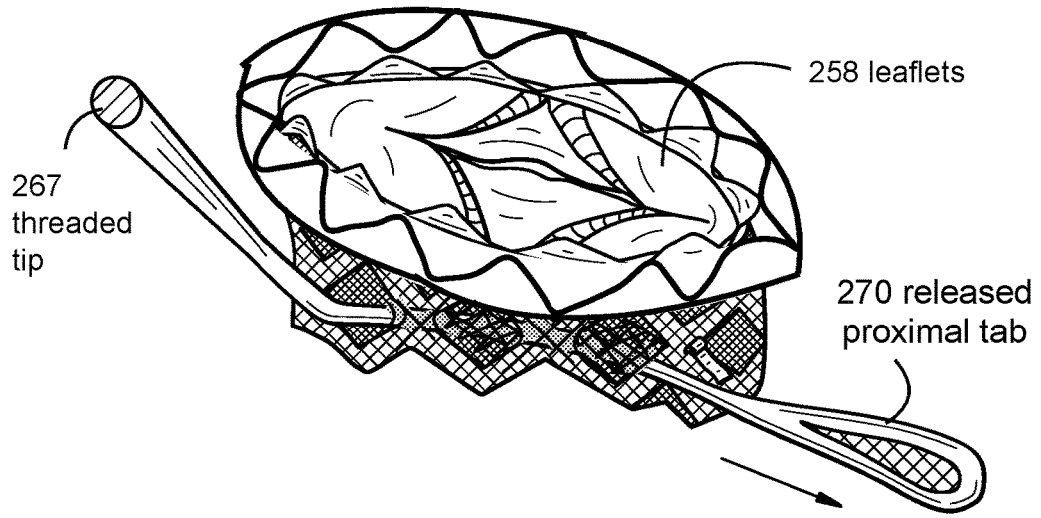
FIG. 7 is an illustration of a SIDE PERSPECTIVE view of a side delivered transcatheter heart valve with superelastic wire loop distal tab and a superelastic wire loop proximal tab in a post-release, extended configuration according to the invention.

FIG. 7 is an illustration of a SIDE PERSPECTIVE view of a side delivered transcatheter heart valve 100 with superelastic wire loop distal tab 268 and a superelastic wire loop proximal tab 270 in a post-release, extended configuration according to the invention. FIG. 7 also shows the threaded atraumatic ball tip 267 at the distal end of the distal tab. FIG. 7 shows that the prosthetic leaflets 258 (2-, 3-, or 4-) are mounted with the channel 104 and leaflets 258 plus any inner support frame and mounting features comprise the flow control component 130.

Figure 8:
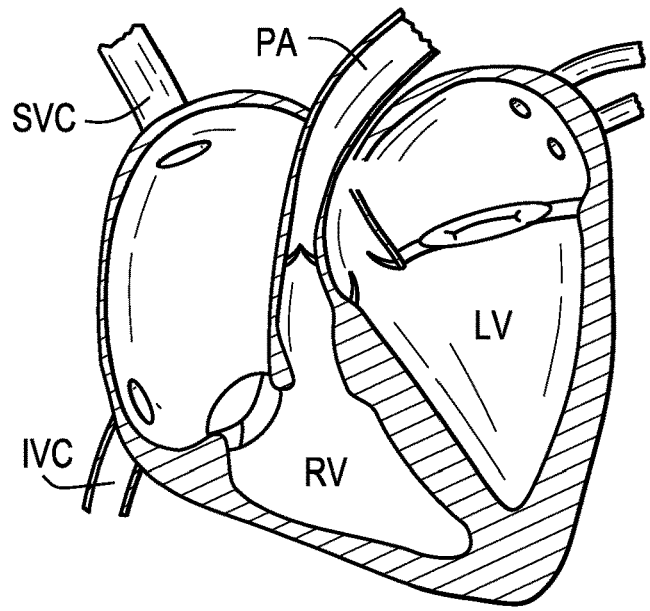
FIG. 8 is an illustration of a SIDE view of human heart anatomy, with an inset showing the geometric relationship between the inferior vena cava (IVC), the three leaflet cusps of the tricuspid valve—anterior, posterior, septal—the right ventricular outflow tract (RVOT), and the pulmonary artery (PA).

FIG. 8 is an illustration of a SIDE view of human heart anatomy, with an inset showing the geometric relationship between the inferior vena cava (IVC), the three leaflet cusps of the tricuspid valve—anterior, posterior, septal—the right ventricular outflow tract (RVOT), and the pulmonary artery (PA).

FIG. 9 is an illustration of a ANTERIOR SIDE PERSPECTIVE view of a side delivered valve 100 seated with the native tricuspid annulus with collar portion 105 laying atrially above the tricuspid annulus and leaflets, lower body portion 106 extending into and through the annulus to provide corrective hemodynamic flow from the flow control component, and distal RVOT footer anchoring tab 268, proximal anchoring tab 270, and tension arm extender wire 265 connecting the distal tab 268 and the proximal tab 270.

FIG. 10 is an illustration of a SEPTAL SIDE PERSPECTIVE view of a side delivered valve 100 seated with the native tricuspid annulus with collar portion 105 laying atrially above the tricuspid annulus and leaflets, lower body portion 106 extending into and through the annulus to provide corrective hemodynamic flow from the flow control component, and distal RVOT footer anchoring tab 268, proximal anchoring tab 270, and tension arm extender wire 265 connecting the distal tab 268 and the proximal tab 270.

FIG. 11 is an illustration of a PROXIMAL SIDE VIEW of the valve 100 with proximal tab 270 extending toward the viewer out of the page.

FIG. 12 is an illustration of a DISTAL SIDE VIEW of the valve 100 with distal tab 268 extending toward the viewer out of the page.

FIG. 13 is an illustration of a SIDE VIEW of a valve according to the invention with a guide wire 311 threading through a distal tab tip element 267, and a pusher tube 310 extending from a delivery catheter 138, the pusher tube 310 sheathed over the guide wire 311 but unable to pass the tip element 267 thereby providing a mechanism for pulling the valve 100 out of the delivery catheter 138 from the distal side to avoid damaging compressive pushing forces that usually attend the expelling process of a standard prosthetic valve from a delivery catheter 138.

FIGS. 14-15-16-17 are illustrations of a SEPTAL SIDE VIEW of a process whereby a compressed valve 136 is delivered via catheter 138, the compressed valve 136 is partially ejected and allowed to partially self-expand to establish blood flow around and through the valve, the valve is then seated into the native annulus, and finally the proximal tab 270 is detached from its securement mechanism and the proximal tab 270 and the distal tab 268 provide sub-annular anchoring.

FIGS. 18-19-20-21 are illustrations of an ANTERIOR SIDE VIEW of a process whereby a compressed valve 136 is delivered via catheter 138, the compressed valve 136 is partially ejected and allowed to partially self-expand to establish blood flow around and through the valve, the valve is then seated into the native annulus, and finally the proximal tab 270 is detached from its securement mechanism and the proximal tab 270 and the distal tab 268 provide sub-annular anchoring.

FIGS. 22-23-24-25 are illustrations of a SEPTAL SIDE VIEW of a process whereby a compressed laser cut valve 136 is delivered via catheter 138, the compressed valve 136 is partially ejected and allowed to partially self-expand to establish blood flow around and through the valve, the valve is then seated into the native annulus, and finally the proximal tab 270 is detached from its securement mechanism and the proximal tab 270 and the distal tab 268 provide sub-annular anchoring.

FIGS. 26-27-28-29-30 are illustrations of a SEPTAL SIDE VIEW of a process whereby a guide wire 311 is initially deployed into the pulmonary artery, the compressed valve 136 is delivered via catheter 138, the compressed valve 136 is partially ejected and allowed to partially self-expand to establish blood flow around and through the valve, the valve is then seated into the native annulus, and finally the proximal tab 270 is detached from its securement mechanism and the proximal tab 270 and the distal tab 268 provide sub-annular anchoring.

FIG. 31 is an illustration of a TOP ANTERIOR VIEW of a valve according to the present invention with the dual tab mechanism (distal and proximal) 268+265+270 attached around the circumference of the body portion 106 of the valve, beneath the collar portion 105.

FIG. 32 is an illustration of a TOP SEPTAL VIEW of a valve according to the present invention with the dual tab mechanism (distal and proximal) 268+265+270 attached around the circumference of the body portion 106 of the valve, beneath the collar portion 105.

FIG. 33 is an illustration of a SIDE VIEW of a heart with a delivery catheter having a compressed valve 136 where a distal tab element 268 is threaded onto the guide wire 311 leading up the femoral vein through the IVC, a pusher or valve advancing tool 310 is a sheath on the guide wire 311, and the system is ready to be delivered to the left atrium.

FIG. 34 is an illustration of a SIDE VIEW of a heart having a delivery catheter 138 advanced transeptally to the left atrium from the femoral/IVC access, and valve advancing tool 310 is positioning the distal tab 268 in the sub-annular mitral antero-lateral commissure anchoring area.

FIG. 35 is an illustration of a SIDE VIEW of a heart having a side delivered mitral valve prosthesis according to the present invention, with the transeptal stitch closing the access point.

FIG. 36 is an illustration of a TOP VIEW a side delivered valve positioned relative to the native mitral annulus and shows how distal tab 268 and proximal tab 270 provide anchoring in the A1-P1 and A3-P3 commissural anchoring areas.

FIG. 37 is an illustration of a TOP VIEW of a native valve annulus in solid line with a prosthetic valve 100 in dashed line.

FIG. 38 is an illustration of a SIDE VIEW from the anterior side of the mitral annulus of a side delivered valve positioned relative to the native mitral annulus and shows how distal tab 268 and proximal tab 270 provide anchoring in the A1-P1 and A3-P3 commissural anchoring FIG. 39 is an illustration of a SIDE VIEW of a native valve annulus in solid line with a prosthetic valve in dashed line.

FIG. 40-41-42-43 are illustrations of a proximal tab 270 fold and release mechanism 275, either using a mechanical hinge or similar mechanism, or using the spring (shape-memory) aspect of the superelastic material.

FIG. 44 is an illustration of a TOP VIEW a side delivered valve positioned relative to the native tricuspid annulus and shows how distal tab 268 and proximal tab 270 provide anchoring in the distal (RVOT) and proximal (adjacent IVC) anchoring areas.

FIG. 45 is an illustration of a TOP VIEW of a native valve annulus in solid line with a prosthetic valve in dashed line.

FIG. 46 is an illustration of a SIDE PERSPECTIVE VIEW of a valve having multiple, e.g. 3 or more, sub-annular anchoring tabs 268+270+269.

FIG. 47 is a text flow chart showing process steps of one preferred method of delivery of an orthogonally compressed, delivered, transitioned, and released prosthetic valve. FIG. 47 shows a process in steps for an Orthogonal Valve Delivery Process:

(i) advance guide wire to pulmonary artery or a left ventricle using femoral vein or brachiocephalic vein, extend through IVC or SVC, and extend to the pulmonary artery or left ventricle;

(ii) advance delivery catheter over the guide wire to right atrium of the tricuspid valve or a left atrium of the mitral valve;

(iii) advance and deliver an orthogonally compressed self-expandable prosthetic heart valve to the atrium (iv) partially release valve from the delivery catheter by advancing sheath over the guide wire, and position the distal anchoring tab at RVOT or a sub-annular area below antero-lateral commissure of a mitral valve, and hold the valve at a raised angle >30 degrees to a localized annular plane relative to the horizontal axis of the valve and the delivery catheter, to permit blood flow around and through the prosthetic valve to provide a gradual blood flow transition from flow through native leaflets to complete flow through the prosthetic valve (v) complete release of the valve from delivery catheter and seat the valve in the native annulus by applying a downward force in the direction of the ventricle; and (vi) seating at least one proximal anchoring tab at a second desired proximal anchoring area.

PARTS LIST

Below is provide a parts list in relation to claimed elements. Part numbering may refer to functional components and may be re-used across differing preferred embodiments to aid in uniformly understanding structure-function relationships. To avoid cluttering in drawing sheets, not every number may be added to the drawing sheets, or may be added later during examination as needed.

100 An dual-tab side delivered transcatheter prosthetic heart valve
102 FRAME a self-expanding annular support frame
104 CHANNEL a central channel and
105 COLLAR collar
106 BODY (TRANS-ANNULAR) WALL an outer perimeter wall
108 CENTRAL AXIS
110 ANTERIOR WALL
112 POSTERIOR-SEPTAL WALL
114 PROX SIDE
116 PROX FOLD
117 second PROX FLD
118 DISTAL SIDE
120 DISTAL FOLD
121 SECONDARY DISTAL FOLD
122 ANTERIOR COLLAR
124 ANTERIOR BODY
126 POSTERIOR-SEPTAL COLLAR
128 POSTERIOR-SEPTAL BODY
130 FLOW CONTROL COMPONENT
132 INFLOW END
134 OUTFLOW END
136 COMPRESSED CONFIG
138 DELIVERY CATHETER
139 DELIVERY CATH, distal end
140 HORIZ AXIS a horizontal axis at
142 an intersecting angle of between 45-135 degrees to the central vertical axis
144 EXPANDED CONFIG
146 CYLINDER AXIS
148 a height of about 5-60 mm and
150 a diameter of about 25-80 mm.
202 WIRE CELLS
204 GEOMETRY orthogonal to the central vertical axis to minimize wire cell strain
206 COMPRESSED CONFIG, e.g. a vertical compressed
208 ROLLED COMPRESSED CONFIG
210 FOLDED COMPRESSED CONFIG
211 ROLLED FLOW CONTROL rolled flow control component
212 a SHAPE OF BODY portion selected from a funnel, cylinder, flat cone, or circular hyperboloid
220 a braided frame,
222 wire frame, or
224 laser-cut wire frame,
226 a biocompatible material.
228 a side profile of valve body is a flat cone shape
230 a diameter R of 40-80 mm,
232 a diameter r of 20-60 mm, and
234 a height of 5-60 mm.
236 INNER FRAME
238 OUTER SURFACE OF FRAME
240 PERICARDIAL tissue
242 DACRON
244 an hourglass shape having
246 a top diameter R1 of 40-80 mm,
248 a bottom diameter R2 of 50-70 mm,
250 an internal diameter r of 20-60 mm, and
252 a height of 5-60 mm.
254 an internal diameter of 20-60 mm and
256 a height of 10-40 mm, and
258 a plurality of LEAFLETS of pericardial material
260 a ROUNDED cylinder at an INFLOW END and having
262 a FLAT closable aperture at an OUTFLOW END
264 RIBS
265 TENSIONER WIRE CONNECTING TABS
266 TENSION ARM a tension arm extending from a distal side
267 THREADED TIP ELEMENT/BALL tip with eyelet
268 DISTAL SUBANNULAR ANCHORING TAB tab
269 ANY SUBANNULAR ANCHORING TAB
270 PROXIMAL TAB
271 UPPER TENSION ARM an upper tension arm attached to
272 a DISTAL UPPER EDGE of the annular support frame
274 RVOT TAB a lower tension arm
275 FOLDED TAB (stowed, compressed)
276 a DISTAL SIDE of the annular support frame
278 TISSUE ANCHOR
280 a first FLAT PANEL and the back wall portion is
282 a second FLAT PANEL,
284 SEAM, HINGE a sewn seam, a fabric panel, or a rigid hinge.
286 a flexible FABRIC SPAN without any wire cells proximal fold area and the distal fold area.
288 braided-wire cells,
290 laser-cut wire cells,
292 photolithography produced wire cells,
294 3D printed wire cells,
296 WAVE SHAPE wire cells formed from intermittently connected single strand wires in a wave shape,
297 HORIZ WAVE SHAPE CELLS
298 ZIG-ZAG/DIAMOND shape
300 SPIRAL OUTER FRAME shape, and combinations thereof.
301 asymmetric, irregular rounded cells, compressed
303 asymmetric, irregular rounded cells, expanded
305 ONE-PIECE FOLDABLE OUTER FRAME
307 COMBINATION OF MULTIPLE CELL TYPES
302 (i) unilaterally rolling to a compressed
304 (ii) bilaterally rolling
306 (iii) flattening the frame into parallel panels
308 (iv) flattening the frame along a vertical axis
310 RIGID PUSH/PULL ROD rigid catheter, valve deployment element
311 GUIDE WIRE
312 a STEERABLE CATHETER
314 a TAPERING FIXTURE or funnel
316 a LOADING ACCESSORY
318 LOADING PUSHING ROD OR PULLING WIRE
320 a COMPRESSION ELEMENT on an inner surface of the tapering fixture
402 PARTIAL partial open configuration
404 EXPANDED UNMOUNTED completely open unmounted configuration
406 MOUNTED EXPANDED mounted valve
408 attachment point
410 release mechanism
412 release wire Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A method for delivering a prosthetic heart valve to an annulus of a native valve between a ventricle and an atrium of a heart, the method comprising the steps:
   (i) disposing in the atrium of the heart a distal portion of a delivery catheter having a lumen and a longitudinal axis, with a distal end of the delivery catheter directed towards the annulus of the native valve, the distal portion of the delivery catheter having disposed within the lumen thereof the prosthetic heart valve in a compressed configuration,
   wherein the compressed configuration of the prosthetic heart valve has a long-axis substantially parallel to a length-wise cylindrical axis of the delivery catheter,
   wherein the expanded configuration of the prosthetic heart valve has a height of about 5-60 mm and a diameter of about 25-80 mm,
   wherein the prosthetic heart valve comprises an annular support frame having a flow control component mounted within the annular support frame and configured to permit blood flow in a first direction through an inflow end of the valve and block blood flow in a second direction, opposite the first direction, through an outflow end of the valve,
   wherein the annular support frame is self-expanding or balloon-expandable,
   a distal anchoring tab is mounted on a distal side of the annular support frame, the distal anchoring tab having a length of 10-40 mm, the distal anchoring tab extending laterally from the annular support frame and is configured to be disposed on a ventricle side of the annulus of the native valve when the annular support frame is disposed within the annulus,
   at least one proximal anchoring tab is mounted on a proximal side of the annular support frame, the proximal anchoring tab having a length of 2-25 mm, the at least one proximal anchoring tab extending laterally from the annular support frame and is configured to be disposed on the ventricle side of the annulus of the native valve when the annular support frame is disposed within the annulus;
   (ii) partially releasing the prosthetic heart valve from the delivery catheter, and positioning the distal anchoring tab at a distal subannular anchoring area, wherein positioning the distal anchoring tab holds the prosthetic heart valve at a raised angle of at least 30 degrees to a localized annular plane relative to a horizontal axis of the valve, and
   wherein partially releasing the prosthetic heart valve permits blood to flow partially around the prosthetic heart valve and through the native leaflets, and partially through the flow control component of the prosthetic valve to provide a gradual blood flow transition from flow through native leaflets to complete flow through the prosthetic valve,
   wherein the distal subannular anchoring area is a right ventricular outflow tract (RVOT) of a right ventricle or is a sub-annular area below an A1-P1 antero-lateral commissure of a mitral valve;
   (iii) completing release of the entire prosthetic heart valve from within the lumen of the delivery catheter, and seating the prosthetic heart valve in the native annulus by applying a downward force in the direction of the ventricle; and
   (iv) seating the proximal anchoring tab at a proximal subannular anchoring area.

2. The method of claim 1, comprising the additional step of anchoring one or more tissue anchors attached to the valve into native tissue.

3. The method of claim 1 wherein seating the proximal anchoring tab comprises releasing the proximal anchoring tab from a compressed pre-release configuration to an expanded post-release configuration with the proximal anchoring tab extending into the proximal subannular anchoring area.

4. A method for orthogonal delivery of implantable prosthetic heart valve in the body, the method comprising the steps:
   (i) advancing a distal end of a guide wire to a distal location, wherein the distal location is a pulmonary artery or a left ventricle of a heart, wherein the guide wire starts outside of a patient using femoral vein access or brachiocephalic vein access, and extends through an inferior vena cava or a superior vena cava to a right atrium, and extends from the right atrium through the tricupsid valve to the pulmonary artery or extends from the right atrium across the atrial septum in a transeptal access through the mitral valve and into a left ventricle;
   (ii) advancing a delivery catheter over the guide wire to a target location, where the target location is a right atrium of the tricuspid valve or a left atrium of the mitral valve;
   (iii) advancing and delivering an orthogonally compressed self-expandable prosthetic heart valve to the target location in the body,
   wherein a compressed configuration of the valve has a long-axis substantially parallel to a length-wise cylindrical axis of the delivery catheter,
   wherein the expanded configuration of the valve has a height of about 5-60 mm and a diameter of about 25-80 mm,
   wherein the valve comprises an annular support frame having a flow control component mounted within the annular support frame and configured to permit blood flow in a first direction through an inflow end of the valve and block blood flow in a second direction, opposite the first direction, through an outflow end of the valve,
   a distal anchoring tab is mounted on a distal side of the annular support frame, the distal anchoring tab having a length of 10-40 mm and a width of 2-10 mm, wherein the guide wire is threaded through a threading aperture on or within the distal anchoring tab,
   at least one proximal anchoring tab is mounted on a proximal side of the annular support frame, the proximal anchoring tab having a length of 2-25 mm and a width of 2-10 mm, and
   a valve advancing tool comprising an elongated sheath wherein the guide wire is within a lumen of the sheath, wherein the outer diameter of the sheath is larger than the inner diameter of the threading aperture on the distal anchoring tab, wherein when the sheath is advanced over the guide wire in a distal direction, and a distal end of the sheath contacts a proximal surface of the threading aperture, the valve is advanced distally through the delivery catheter by the distally-directed pulling force that the sheath imparts to the distal anchoring tab;

(iv) partially releasing the valve from the delivery catheter by advancing the sheath over the guide wire, and positioning the distal anchoring tab at a desired anchoring area of the target location, wherein the desired anchoring area is selected from a right ventricular outflow tract (RVOT) of a right ventricle, and a sub-annular area below an A1-P1 antero-lateral commissure of a mitral valve, wherein positioning the distal anchoring tab holds the valve at a raised angle of at least 30 degrees to a localized annular plane relative to the horizontal axis of the valve and the delivery catheter, wherein partially releasing the valve permits blood to flow partially around the prosthetic valve and through the native leaflets, and partially through the flow control component of the prosthetic valve to provide a gradual blood flow transition from flow through native leaflets to complete flow through the prosthetic valve;

(v) completing release of the entire valve from the delivery catheter by advancing the sheath over the guide wire, seating the valve in the native annulus by applying a downward force in the direction of the ventricle; and (vi) seating the at least one proximal anchoring tab at a second desired anchoring area.

5. The method of claim 4, comprising the additional step of anchoring one or more tissue anchors attached to the valve into native tissue.

* * * * *